(12) United States Patent
Coats et al.

(10) Patent No.: US 7,408,008 B2
(45) Date of Patent: Aug. 5, 2008

(54) METHOD OF PRODUCING HIGHLY FUNCTIONALIZED 1,3-DIAMINO-PROPAN-2-OLS FROM SOLID SUPPORT

(75) Inventors: Steve J. Coats, Quakertown, PA (US); Dennis J. Hlasta, Doylestown, PA (US); Mark J. Schulz, Skippack, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 605 days.

(21) Appl. No.: 11/006,145

(22) Filed: Dec. 7, 2004

(65) Prior Publication Data

US 2005/0124001 A1    Jun. 9, 2005

Related U.S. Application Data

(60) Provisional application No. 60/527,963, filed on Dec. 9, 2003.

(51) Int. Cl.
*C08F 8/30* (2006.01)
(52) U.S. Cl. .................... 525/333.6; 549/552
(58) Field of Classification Search ............. 525/333.6; 549/512, 552; 435/7.1
See application file for complete search history.

(56) References Cited

U.S. PATENT DOCUMENTS 6,150,416 A    11/2000    Kick et al.

OTHER PUBLICATIONS

Baker, C.T. et al.:: Design, Synthesis, and Conformational Analysis of a Novel Series of HIV Protease Inhibitors; Biorg. & Med. Chem. Letters (1998) 8: 3631-3636.
Berge, S.M. et al.: Pharmaceutical Salts; J. of Pharmaceutical Salts; J. of Pharmaceutical Sciences (1977) 66(1): 1-19.
Chino, M. et al.: Efficient method to prepare hydroxyethylamine-based aspartyl protease inhibitors with diverse $P_1$ side chains; Tetrahedron (2002) 58: 6305-6310.
Dörner, B. et al.: The Synthesis of Peptidomimetic Combinatorial Libraries Through Successive Amide Alkylations; Bioorg. & Med. Chem. (1996) 4(5): 709-715.
Gould, P.L.: Salt selection for basic drugs; Intl J. of Pharmaceutics (1986) 33: 201-217.
Kick, E.K. et al.: Expedient Method for the Solid-Phase Synthesis of Aspartic Acid Protease Inhibitors Directed toward the Generation of Libraries; J. Med. Chem. (1995) 38: 1427-1430.
Lebon, F. et al.: Approaches to the Design of Effective HIV-1 Protease Inhibitors; Current Med. Chem. (2000) 7: 455-477.
Tamamura, H. et al.: Synthesis of potent β-secretase inhibitors containing a hydroxyethylamine dipeptide isostere and their structure-activity relationship studies; Org. Biomol. Chem. (2003) 1: 2468-2473.

*Primary Examiner*—B. Dentz
*Assistant Examiner*—David E Gallis

(57) ABSTRACT

The invention is directed to compounds and methods of synthesizing hydroxyethlamino amides and their use in treatment of aspartyl protease mediated diseases and conditions.

3 Claims, No Drawings

METHOD OF PRODUCING HIGHLY FUNCTIONALIZED 1,3-DIAMINO-PROPAN-2-OLS FROM SOLID SUPPORT

CROSS-REFERENCE TO RELATED APPLICATIONS

This application claims priority to U.S. Provisional Application 60/527,963 filed Dec. 9, 2003 and hereby fully incorporated by reference.

STATEMENT REGARDING FEDERALLY SPONSORED RESEARCH OR DEVELOPMENT

The research and development of the invention described below was not federally sponsored.

BACKGROUND OF THE INVENTION

The present invention is directed to synthetic routes to prepare aspartic protease inhibitors and in particular, hydroxyethyl amine inhibitors. The present invention is also directed to synthetic intermediates along those routes, and to the inhibitors, themselves. The use of parallel synthetic sequences to prepare focused chemical libraries directed toward a specific protein family, when leveraged by a suitably broad synthetic method, is a highly valuable approach for hit generation in drug discovery because a hit to any member of that protein family may be identified and the speed in which analogs may be prepared in a subsequent hit to lead program is substantially increased.

The aspartyl protease family includes: HIV protease, cathepsins, β-secretase, renin, and plasmepsin. A number of native and enzyme-inhibitor crystal structures have been solved for the above aspartic proteases. A key structural element in most inhibitors is a hydroxyl or hydroxyl like moiety that binds to the catalytically active aspartic acids in the enzyme active site. Work toward the development of mechanism pathway inhibitors for this family of enzymes has resulted in the identification of a number of transition-state analogue units, which are effective for inhibiting aspartic proteases.

Two of the most useful of these transition-state analogue units are the hydroxyethylene and hydroxyethylamine units; the later isostere has been employed extensively in agents for the treatment of AIDS and are currently used in clinical practice (Lebon, F.; Ledecq, M. Curr. Med. Chem. 2000, 7, 455-477).

Other solid-phase and/or parallel approaches to synthesis of hydroxyethyl amines have been described. Tamamura, H. et al., Org. Biomol. Chem. 2003, 1, 2468-2473 describe a solid phase synthesis of hydroxyethylamine dipeptide isosteres but do not describe or suggest the methods or compounds of the present invention. U.S. Pat. No. 6,150,416 to Kick et al. describes hydroxyethylamine compounds that bind cathepsin D, but does not describe or suggest the methods or compounds of the present invention. Kick, E. K.; Ellman, J. A. J. Med. Chem. 1995, 38, 1427-1430 describe the solid phase synthesis of hydroxyethylamino aspartyl protease inhibitors, but does not describe or suggest the methods or compounds of the present invention. Baker, C. T. et al., Bioorg. Med. Chem. Lett. 1998, 8, 3631-3636 also describe the solid phase synthesis of hydroxyethylamino aspartyl protease inhibitors, but does not describe or suggest the methods or compounds of the present invention. Chino, M. et al., Tetrahedron 2002, 58, 6305-6310 also describe the solid phase synthesis of hydroxyethylamino aspartyl protease inhibitors, but does not describe or suggest the methods or compounds of the present invention. None of these prior approaches provides as flexible or efficient a means of synthesizing hydroxyethyl amines as does the present invention.

Dörner, B. et al. (Bioorg. Med. Chem. 1996, 4, 709-715) describe a solid-phase synthetic method for generating alkylated amides using nine successive cycles exposing a support-bound amide to lithium tert-butoxide followed by quenching with electrophile. Such a method, however, cannot provide the epoxyalkyl intermediates useful in the present invention in practical yields.

Thus, a solid phase method has been developed to generate hydroxyethylamino amides, a known aspartyl protease isostere. We have preformed the eight step sequence and obtained the resulting hydroxyethylamino amides in good yield without the need for rigorous exclusion of water or oxygen. The procedure draws on large reagent pools: carboxylic acids, 1° amines, and aldehydes; which results in a virtual library of over 1 trillion compounds. In addition, we have developed a general method for the monoalkylation of Rink type resins.

SUMMARY OF THE INVENTION

The present invention is directed to methods of synthesizing a hydroxyethlamino amide of Formula (I):

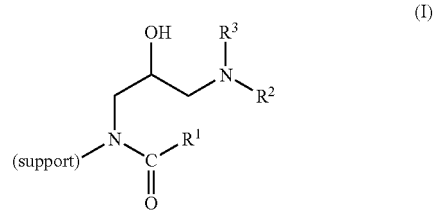

wherein:
$R^1$ is $C_{1-8}$alkanyl, cyclic$C_{1-8}$alkanyl, $C_{6-14}$aryl, $C_{5-14}$heteroaryl $C_{2-8}$alkenyl, $C_{1-8}$alkoxy($C_{2-8}$)alkenyl, $C_{2-8}$alkynyl, $C_{1-8}$alkoxy($C_{2-8}$)alkynyl, heteroaryl($C_{2-8}$)alkenyl, or heteroaryl($C_{2-8}$)alkynyl; wherein said $C_{1-8}$alkanyl, cyclic$C_{1-8}$alkanyl, $C_{6-14}$aryl, $C_{5-14}$heteroaryl $C_{2-8}$alkenyl, $C_{1-8}$alkoxy($C_{2-8}$)alkenyl, $C_{2-8}$alkynyl, $C_{1-8}$alkoxy($C_{2-8}$) alkynyl, heteroaryl($C_{2-8}$)alkenyl, and heteroaryl($C_{2-8}$) alkynyl are optionally substituted with one to two substituents independently selected from the group consisting of $C_{6-14}$aryloxy, di$C_{1-8}$alkanylamino, $C_{1-8}$alkanylamino, $C_{1-8}$alkanyl, $C_{6-14}$aryl, $C_{1-8}$alkanyloxy, $C_{1-8}$alkanylcarbonyl, perhalo$C_{1-6}$alkanyl, halo, $C_{5-14}$heteroaryl, $C_{1-8}$alkanyl, $C_{1-8}$alkanylthio, oxo$C_{5-8}$cyclicheteroalkenyl, $C_{6-14}$arylalkynyl, $C_{1-8}$alkanylsulfonyl, $C_{6-14}$aryl$C_{1-8}$alkanyl, $C_{1-8}$alkanyloxy, $C_{6-14}$aryl$C_{1-8}$alkanyloxy, $C_{6-14}$aryl$C_{1-8}$alkanyloxycarbonylamino, and $C_{1-8}$alkanylcarbonylamino;

$R^2$ is $C_{1-8}$alkanyl, $C_{2-8}$alkenyl, $C_{1-8}$alkoxy($C_{2-8}$)alkenyl, $C_{2-8}$alkynyl, $C_{1-8}$alkanyloxy($C_{2-8}$)alkynyl, heteroaryl ($C_{2-8}$) alkenyl, heteroaryl($C_{2-8}$)alkynyl hydrogen, or N-linked-$C_{1-8}$alkanylcarbonylamino, wherein the $C_{1-8}$alkanyl, $C_{1-8}$alkenyl $C_{2-8}$alkynyl portions of $R^2$ are optionally substituted with one or two substituents independently selected from the group consisting of $C_{1-8}$alkanyl$C_{1-14}$aryl, $C_{1-8}$alkanyloxy$C_{6-14}$aryl, $C_{5-14}$heteroaryl, $C_{6-14}$aryl, or $C_{6-14}$aryl;

$R^3$ is $C_{1-8}$alkanyl, $C_{2-8}$alkenyl, $C_{1-8}$alkoxy($C_{2-8}$)alkenyl, $C_{2-8}$alkynyl, $C_{1-8}$alkoxy($C_{2-8}$)alkynyl, heteroaryl($C_{2-8}$)

alkenyl, heteroaryl($C_{2-8}$)alkynyl, $C_{1-8}$alkanyl, cyclic$C_{1-8}$alkanyl, $C_{6-14}$aryl, or $C_{5-14}$heteroaryl; wherein said $C_{1-8}$alkanyl, cyclic$C_{1-8}$alkanyl, $C_{6-14}$aryl, and $C_{5-14}$heteroaryl is optionally and independently substituted with one or two substituent selected from the group consisting of ($C_{1-8}$alkanylthio)(aminocarbonyl), $C_{1-8}$alkanylaminocarbonyl, ($C_{6-14}$aryl)($C_{1-8}$alkanylaminocarbonyl), amino, aminosulfonyl$C_{6-14}$aryl, $C_{1-8}$alkanyl$C_{3-8}$cyclicheteroalkanyl, $C_{1-8}$alkanyloxycarbonylamino, $C_{1-8}$alkanyl$C_{6-14}$arylamino, $C_{1-8}$alkanyl$C_{6-14}$aryl, $C_{1-8}$alkanyloxy$C_{6-14}$aryl, $C_{3-8}$cyclicheteroalkanyl, $C_{6-14}$aryl, $C_{6-14}$aryl$C_{1-8}$alkanyloxycarbonylamino, $C_{6-14}$aryloxy, $C_{6-14}$aryloxy$C_{6-14}$aryl, di$C_{1-8}$alkanyloxy$C_{6-14}$aryl, dihalo$C_{6-14}$aryl halo$C_{6-14}$aryl, and oxo$C_{3-8}$cyclicheteroalkanyl; $C_{6-14}$aryl wherein said aryl is optionally and independently substituted with a substituent selected from the group consisting of $C_{1-8}$alkanyl, and $C_{6-14}$aryloxy; $C_{1-8}$alkanyl$C_{3-8}$cyclicheteroalkanyl; $C_{5-14}$heteroaryl; $C_{6-14}$aryl$C_{1-8}$alkanylheteroalkanyl; or $C_{3-8}$cyclicheteroalkanyl; and and enantiomers, diastereomers, tautomers, solvates, or pharmaceutically acceptable salts thereof, the method comprising:

(a) preparing a epoxymethylated support of formula (Ia)

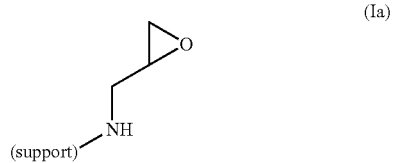

(Ia)

wherein (support) is selected from the group consisting of amine based polystyrene resins;

(b) reacting the support of formula (Ia) with an $R^1$ carboxylic acid or derivative of the formula $R^1COY$ wherein Y is OH, Cl, Br, $OC_{1-3}$alkanyl or $OOCR^1$ to generate an epoxymethylated amido support of formula (Ib)

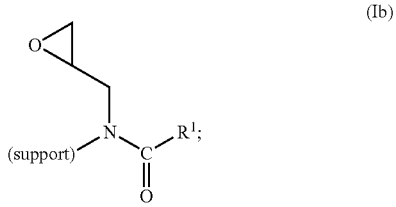

(Ib)

(c) reacting the epoxymethylated amido support of formula (Ib) with an $R^2$ amine of the formula $R^2NH_2$ to generate a hydroxyethlamino amido support of formula (Ic)

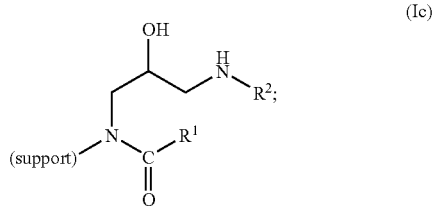

(Ic)

(d) reacting the hydroxyethlamino amido support of formula (Ic) with an $R^3$ aldehyde of the formula $R^3CHO$ to generate a hydroxyethlamino amido support of formula (Id)

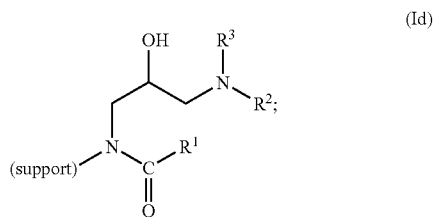

(Id)

and (e) cleaving the hydroxyethlamino amide of formula (I) from the hydroxyethlamino amido support of formula (Id).

The present invention is also directed to pharmaceutical compositions containing compounds of Formula (I).

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive, or in the case of a radical with heteroatoms, refers to a radical containing from a to b atoms including both carbon and heteroatoms. For example, $C_{1-3}$alkanyl denotes a an alkanyl radical containing 1, 2 or 3 carbon atoms, and $C_{4-7}$heteroalkanyl denotes a heteroalkanyl containing from 4 to 7 atoms including both carbon atoms and heteroatoms.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl ( ), prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$) alkyl, with ($C_1$-$C_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene.

The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or (C$_1$-C$_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C$_{5-20}$) aryl, with (C$_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. [In preferred embodiments, the arylalkyl group is (C$_{6-26}$) arylalkyl, e.g., the alkanyl, alkenyl or alkynyl moiety of the arylalkyl group is (C$_{1-6}$) and the aryl moiety is (C$_{5-20}$). In particularly preferred embodiments the arylalkyl group is (C$_{6-13}$), e.g., the alkanyl, alkenyl or alkynyl moiety of the arylalkyl group is (C$_{1-3}$) and the aryl moiety is (C$_{5-10}$). Even more preferred arylalkyl groups arephenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy (CH$_3$CH$_2$CH$_2$O—), propan-2-yloxy ((CH$_3$)$_2$CHO—), cyclopropan-1-yloxy, etc.; butyanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are (C$_{1-8}$) alkanyloxy groups, with (C$_{1-3}$) being particularly preferred.

"Parent Heteroaromatic Ring System:" refers to a parent aromatic ring system in which one carbon atom is replaced with a heteroatom. Heteratoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine., oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cyclicheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cyclicheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cyclicheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O$^-$, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, C$_{1-8}$alkyl, C$_{1-8}$alkanyloxy, fluorinated alkanyloxy, fluorinated alkyl, C$_{1-8}$alkylthio, C$_{3-8}$cycloalkyl, C$_{3-8}$cycloalkanyloxy, nitro, amino, C$_{1-8}$alkylamino, C$_{1-8}$dialkylamino, C$_{3-8}$cycloalkylamino, cyano, carboxy, C$_{1-7}$alkanyloxycarbonyl, C$_{1-7}$alkylcarbonyloxy, formyl, carbamoyl, phenyl, aroyl, carbamoyl, amidino, (C$_{1-8}$alkylamino)carbonyl, (arylamino)carbonyl and aryl(C$_{1-8}$alkyl)carbonyl.

"Support" refers to a solid support suitable for use in solid-phase organic synthesis. Prefered supports are those suitable for use in an automated synthesis apparatus. Suitable supports include amine based polystyrene resins. Most preferred are Rink-type resins, and particularly, Rink-AM resin beads.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenylC$_{1-6}$alkanylaminocarbonylC$_{1-6}$alkyl" substituent refers to a group of the formula

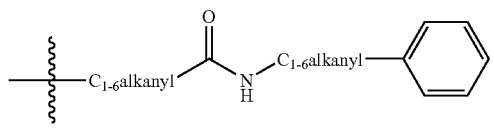

The present invention is directed to methods of synthesizing a hydroxyethlamino amide of Formula (I):

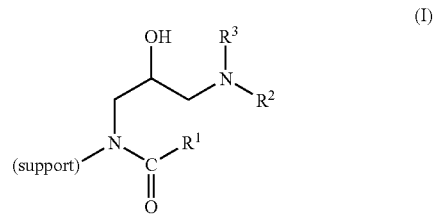

wherein:

R$^1$ is C$_{1-8}$alkanyl, cyclicC$_{1-8}$alkanyl, C$_{6-14}$aryl, C$_{5-14}$heteroaryl C$_{2-8}$alkenyl, C$_{1-8}$alkoxy(C$_{2-8}$)alkenyl, C$_{2-8}$alkynyl, C$_{1-8}$alkoxy(C$_{2-8}$)alkynyl, heteroaryl(C$_{2-8}$)alkenyl, or heteroaryl(C$_{2-8}$)alkynyl; wherein said C$_{1-8}$alkanyl, cyclicC$_{1-8}$alkanyl, C$_{6-14}$aryl, C$_{5-14}$heteroaryl C$_{2-8}$alkenyl, C$_{1-8}$alkoxy(C$_{2-8}$)alkenyl, C$_{2-8}$alkynyl, C$_{1-8}$alkoxy(C$_{2-8}$) alkynyl, heteroaryl(C$_{2-8}$)alkenyl, and heteroaryl(C$_{2-8}$) alkynyl are optionally substituted with one to two substituents independently selected from the group consisting of C$_{6-14}$aryloxy, diC$_{1-8}$alkanylamino, C$_{1-8}$alkanylamino, C$_{1-8}$alkanyl, C$_{6-14}$aryl, C$_{1-8}$alkanyloxy, C$_{1-8}$alkanylcarbonyl, perhaloC$_{1-6}$alkanyl, halo, C$_{5-14}$heteroaryl, C$_{1-8}$alkanyl, C$_{1-8}$alkanylthio, oxoC$_{5-8}$cyclicheteroalkenyl, C$_{6-14}$arylalkynyl, C$_{1-8}$alkanylsulfonyl, C$_{6-14}$arylC$_{1-8}$alkanyl, C$_{1-8}$alkanyloxy, C$_{6-14}$arylC$_{1-8}$alkanyloxy, C$_{6-14}$arylC$_{1-8}$alkanyloxycarbonylamino, and C$_{1-8}$alkanylcarbonylamino;

R$^2$ is C$_{1-6}$alkanyl, C$_{2-8}$alkenyl, C$_{1-8}$alkoxy(C$_{2-8}$)alkenyl, C$_{2-8}$alkynyl, C$_{1-8}$alkanyloxy(C$_{2-8}$)alkynyl, heteroaryl (C$_{2-8}$) alkenyl, heteroaryl(C$_{2-8}$)alkynyl hydrogen, or N-linked-C$_{1-8}$alkanylcarbonylamino, wherein the C$_{1-8}$alkanyl, C$_{1-8}$alkenyl C$_{2-8}$alkynyl portions of R$^2$ are optionally substituted with one or two substituents independently selected from the group consisting of C$_{1-8}$alkanylC$_{6-14}$aryl, C$_{1-8}$alkanyloxyC$_{6-14}$aryl, C$_{5-14}$heteroaryl, C$_{6-14}$aryl, or C$_{6-14}$aryl;

R$^3$ is C$_{1-8}$alkanyl, C$_{2-8}$alkenyl, C$_{1-8}$alkoxy(C$_{2-8}$)alkenyl, C$_{2-8}$alkynyl, C$_{1-8}$alkoxy(C$_{2-8}$)alkynyl, heteroaryl(C$_{2-8}$) alkenyl, heteroaryl(C$_{2-8}$)alkynyl, C$_{1-8}$alkanyl, cyclicC$_{1-8}$alkanyl, C$_{6-14}$aryl, or C$_{5-14}$heteroaryl; wherein said C$_{1-8}$alkanyl, cyclicC$_{1-8}$alkanyl, C$_{6-14}$aryl, and C$_{5-14}$heteroaryl is optionally and independently substituted with one or two substituent selected from the group consisting of (C$_{1-8}$alkanylthio)(aminocarbonyl), C$_{1-8}$alkanylaminocarbonyl, (C$_{6-14}$aryl)(C$_{1-8}$alkanylaminocarbonyl), amino, aminosulfonylC$_{6-14}$aryl, C$_{1-8}$alkanylC$_{3-8}$cyclichetereoalkanyl, C$_{1-8}$alkanyloxycarbonylamino, C$_{1-8}$alkanylC$_{6-14}$arylamino, C$_{1-8}$alkanylC$_{6-14}$aryl, C$_{1-8}$alkanyloxyC$_{6-14}$aryl, C$_{3-8}$cyclicheteroalkanyl, C$_{6-14}$aryl, C$_{6-14}$arylC$_{1-8}$alkanyloxycarbonylamino, C$_{6-14}$aryloxy, C$_{6-14}$aryloxyC$_{6-14}$aryl, diC$_{1-8}$alkanyloxyC$_{6-14}$aryl, dihaloC$_{6-14}$aryl haloC$_{6-14}$aryl, and oxoC$_{3-8}$cyclicheteroalkanyl; C$_{6-14}$aryl wherein said aryl is optionally and independently substituted with a substituent selected from the group consisting of C$_{1-8}$alkanyl, and C$_{6-14}$aryloxy; C$_{1-8}$alkanylC$_{3-8}$cyclicheteroalkanyl; C$_{5-14}$heteroaryl; C$_{6-14}$arylC$_{1-8}$alkanylheteroalkanyl; or C$_{3-8}$cyclicheteroalkanyl; and and enantiomers, diastereomers, tautomers, solvates, or pharmaceutically acceptable salts thereof, the method comprising:

(a) preparing a epoxymethylated support of formula (Ia)

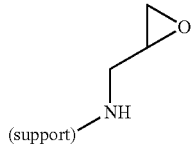

wherein (support) is selected from the group consisting of amine based polystyrene resins;

(b) reacting the support of formula (Ia) with an $R^1$ carboxylic acid or derivative of the formula $R^1COY$ wherein Y is OH, Cl, Br, $OC_{1-3}$alkanyl or $OOCR^1$ to generate an epoxymethylated amido support of formula (Ib)

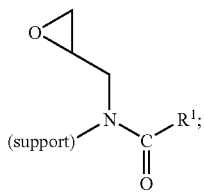

(c) reacting the epoxymethylated amido support of formula (Ib) with an $R^2$ amine of the formula $R^2NH_2$ to generate a hydroxyethlamino amido support of formula (Ic)

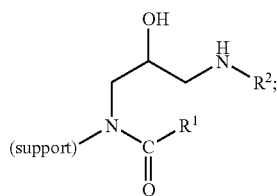

(d) reacting the hydroxyethlamino amido support of formula (Ic) with an $R^3$ aldehyde of the formula $R^3CHO$ to generate a hydroxyethlamino amido support of formula (Id)

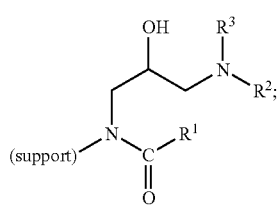

and (e) cleaving the hydroxyethlamino amide of formula (I) from the hydroxyethlamino amido support of formula (Id).

The present invention is also directed to methods of synthesizing a hydroxyethlamino amide of Formula (I):

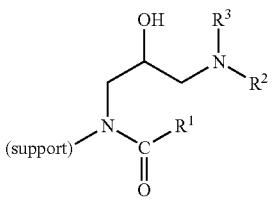

wherein:

$R^1$ is $C_{1-8}$alkanyl, cyclic$C_{1-8}$alkanyl, $C_{6-14}$aryl, or $C_{5-14}$heteroaryl; wherein said $C_{1-8}$alkanyl, cyclic$C_{1-8}$alkanyl, $C_{6-14}$aryl, and $C_{5-14}$heteroaryl are optionally substituted with one to two substituents independently selected from the group consisting of $C_{6-14}$aryloxy, di$C_{1-8}$alkanylamino, $C_{1-8}$alkanylamino, $C_{1-8}$alkanyl, $C_{6-14}$aryl, $C_{1-8}$alkanyloxy, $C_{1-8}$alkanylcarbonyl, perhalo$C_{1-6}$alkanyl, halo, $C_{5-14}$heteroaryl, $C_{1-8}$alkanyl, $C_{1-8}$alkanylthio, oxo$C_{5-8}$cyclicheteroalkenyl, $C_{6-14}$arylalkynyl, $C_{1-8}$alkanylsulfonyl, $C_{6-14}$aryl$C_{1-8}$alkanyl, $C_{1-8}$alkanyloxy, $C_{6-14}$aryl$C_{1-8}$alkanyloxy, $C_{6-14}$aryl$C_{1-8}$alkanyloxycarbonylamino, and $C_{1-8}$alkanylcarbonylamino;

$R^2$ is $C_{1-8}$alkanyl, $C_{1-8}$alkenyl, hydrogen, or N-linked-$C_{1-8}$ alkanylcarbonylamino, wherein said $C_{1-8}$alkanyl and $C_{1-8}$alkenyl are optionally substituted with one or two substituents independently selected from the group consisting of $C_{1-8}$alkanyl$C_{6-14}$aryl, $C_{1-8}$alkanyloxy$C_{6-14}$aryl, $C_{5-14}$heteroaryl, $C_{6-14}$aryl, or $C_{6-14}$aryl;

$R^3$ is $C_{1-8}$alkanyl wherein said $C_{1-8}$alkanyl is optionally and independently substituted with one or two substituent selected from the group consisting of ($C_{1-8}$alkanylthio)(aminocarbonyl), $C_{1-8}$alkanylaminocarbonyl, ($C_{6-14}$aryl)($C_{1-8}$alkanylaminocarbonyl), amino, aminosulfonyl$C_{6-14}$ aryl, $C_{1-8}$alkanyl$C_{3-8}$cyclicheteroalkanyl, $C_{1-8}$alkanyloxycarbonylamino, $C_{1-8}$alkanyl$C_{6-14}$arylamino, $C_{1-8}$alkanyl$C_{6-14}$aryl, $C_{1-8}$alkanyloxy$C_{6-14}$aryl, $C_{3-8}$cyclicheteroalkanyl, $C_{6-14}$aryl, $C_{6-14}$aryl$C_{1-8}$alkanyloxycarbonylamino, $C_{6-14}$aryloxy, $C_{6-14}$aryloxy$C_{6-14}$aryl, di$C_{1-8}$alkanyloxy$C_{6-14}$aryl, dihalo$C_{6-14}$aryl halo$C_{6-14}$aryl, and oxo$C_{3-8}$cyclicheteroalkanyl; $C_{6-14}$aryl wherein said aryl is optionally and independently substituted with a substituent selected from the group consisting of $C_{1-8}$alkanyl, and $C_{6-14}$aryloxy, $C_{1-8}$alkanyl$C_{3-8}$cyclicheteroalkanyl; $C_{5-14}$heteroaryl; $C_{6-14}$aryl$C_{1-8}$alkanylheteroalkanyl; or $C_{3-8}$cyclicheteroalkanyl; and and enantiomers, diastereomers, tautomers, solvates, or pharmaceutically acceptable salts thereof, the method comprising:

(a) preparing a epoxymethylated support of formula (Ia)

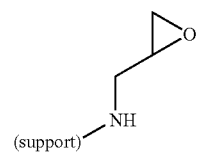

wherein (support) is selected from the group consisting of amine based polystyrene resins;

(b) reacting the support of formula (Ia) with an $R^1$ carboxylic acid or derivative of the formula $R^1COY$ wherein Y is OH, Cl, Br, $OC_{1-3}$alkanyl or $OOCR^1$ to generate an epoxymethylated amido support of formula (Ib)

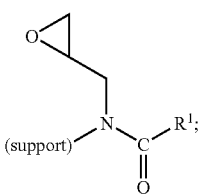

(Ib)

(c) reacting the epoxymethylated amido support of formula (Ib) with an $R^2$ amine of the formula $R^2NH_2$ to generate a hydroxyethlamino amido support of formula (Ic)

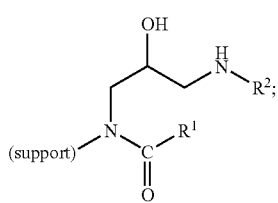

(Ic)

(d) reacting the hydroxyethlamino amido support of formula (Ic) with an $R^3$ aldehyde of the formula $R^3CHO$ to generate a hydroxyethlamino amido support of formula (Id)

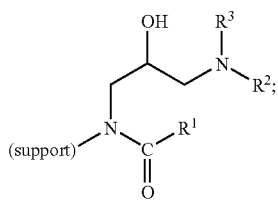

(Id)

and (e) cleaving the hydroxyethlamino amide of formula (I) from the hydroxyethlamino amido support of formula (Id).

Embodiments of the present invention include those wherein:

(a) Y is OH;
(b) (support) is selected from the group consisting of amine based polystyrene resins;
(c) (support) is a Rink-type resin;
(d) (support) is Rink-AM resin;
(e) the alkanyl in substituted $C_{1-8}$alkanyl and $C_{1-8}$alkanyl-substituted substituents is methyl or ethyl;
(f) the aryl in substituted and unsubstituted $C_{6-14}$aryl substituents is phenyl or naphthyl;
(g) the aryl in substituted and unsubstituted $C_{6-14}$aryl substituents is phenyl;
(h) halo is F or Cl;
(i) $R^1$ is optionally substituted phenyl or optionally substituted naphthyl;
(j) $R^1$ is optionally substituted phenyl;
(k) $R^1$ is optionally substituted pyridyl and pyrazinyl, quinolyl, or furyl;
(l) $R^1$ is $C_{6-14}$aryloxy$C_{6-14}$aryl;
(m) $R^1$ is di$C_{1-8}$alkanylamino$C_{6-14}$aryl;
(n) $R^1$ is $C_{1-8}$alkanyl$C_{6-14}$aryl, $C_{6-14}$aryl$C_{1-8}$alkanyl, or di$C_{1-8}$alkanyloxy$C_{6-14}$aryl;
(O) $R^1$ is $C_{1-8}$alkanylcarbonyl$C_{6-14}$aryl;
(p) $R^1$ is perhalo$C_{1-6}$alkanyl$C_{6-14}$aryl;
(q) $R^1$ is halo$C_{5-14}$heteroaryl, or $C_{5-14}$heteroaryl;
(r) $R^1$ is $C_{5-14}$heteroaryl, $C_{1-8}$alkanyl$C_{5-14}$heteroaryl, cyclic$C_{1-8}$alkanyl, or $C_{1-8}$alkanylthio$C_{1-8}$alkanyl;
(s) $R^1$ is oxo$C_{5-8}$cyclicheteroalkenyl;
(t) $R^1$ is $C_{1-8}$alkanyl, or $C_{6-14}$arylalkynyl;
(u) $R^1$ is $C_{1-8}$alkanylsulfonyl$C_{1-8}$alkanyl;
(v) $R^1$ is $C_{6-14}$aryl$C_{1-8}$alkanyl$C_{6-14}$aryl, $C_{1-8}$alkanyloxy$C_{6-14}$aryl, $C_{1-8}$alkanyl$C_{6-14}$aryl, $C_{6-14}$aryl$C_{1-8}$alkanyloxy$C_{6-14}$aryl, $C_{6-14}$aryl$C_{1-8}$alkanyloxycarbonylamino$C_{1-8}$alkanyl, or $C_{1-8}$alkanylcarbonylamino$C_{1-8}$alkanyl;
(w) $R^2$ is $C_{6-14}$aryl$C_{1-8}$alkanyl, di$C_{6-14}$aryl$C_{1-8}$alkanyl, $C_{1-8}$alkanyl, alkenyl, hydrogen, or N-linked-$C_{1-8}$alkanylcarbonylamino;
(x) $R^2$ is $C_{1-8}$alkanyl;
(y) R is $C_{6-14}$aryl$C_{1-8}$alkanyl;
(z) $R^2$ is $C_{1-8}$alkanyl, or $C_{6-14}$aryl$C_{1-8}$alkanyl;
(aa) $R^2$ is hydrogen, $C_{1-8}$alkanyloxy$C_{6-14}$aryl$C_{1-8}$alkanyl;
(bb) R is hydrogen, $C_{1-8}$alkanyloxy$C_{6-14}$aryl$C_{1-8}$alkanyl, or $C_{1-8}$alkanyl$C_{6-14}$aryl$C_{1-8}$alkanyl;
(cc) R is hydrogen;
(dd) R is hydrogen, $C_{1-8}$alkanyl, $C_{5-14}$heteroaryl$C_{1-8}$alkanyl, $C_{6-14}$aryl$C_{1-8}$alkanyl;
(ee) $R^3$ is optionally substituted pyridinyl, thienyl, THF, morpholine, or piperidine;
(ff) $R^3$ is optionally substituted $C_{1-8}$alkanyl;
(gg) $R^3$ is $C_{1-8}$alkanyloxy$C_{6-14}$aryl$C_{1-8}$alkanyl;
(hh) $R^3$ is $C_{1-8}$alkanyloxy$C_{6-14}$aryl$C_{1-8}$alkanyl, dihalo$C_{6-14}$aryl$C_{1-8}$alkanyl, halo$C_{6-14}$aryl$C_{1-8}$alkanyl, di$C_{1-8}$alkanyloxy$C_{6-14}$aryl$C_{1-8}$alkanyl, or $C_{6-14}$aryloxy$C_{6-14}$aryl$C_{1-8}$alkanyl;
(ii) $R^3$ is $C_{1-8}$alkanyl$C_{6-14}$aryl$C_{1-8}$alkanyl, $C_{6-14}$aryl$C_{1-8}$alkanyl, halo$C_{6-14}$aryl$C_{1-8}$alkanyl, $C_{1-8}$alkanyloxy$C_{6-14}$aryl$C_{1-8}$alkanyl, di$C_{1-8}$alkanyloxy$C_{6-14}$aryl$C_{1-8}$alkanyl, or $C_{6-14}$aryloxy$C_{6-14}$aryl$C_{1-8}$alkanyl;
(jj) $R^3$ is $C_{1-8}$alkanyl$C_{6-14}$aryl$C_{1-8}$alkanyl, $C_{6-14}$aryl$C_{1-8}$alkanyl, halo$C_{6-14}$aryl$C_{1-8}$alkanyl, $C_{1-8}$alkanyloxy$C_{6-14}$aryl$C_{1-8}$alkanyl, or $C_{6-14}$aryloxy$C_{6-14}$aryl$C_{1-8}$alkanyl;
(kk) $R^3$ is $C_{6-14}$aryl$C_{1-8}$alkanyl, $C_{1-8}$alkanyloxy$C_{6-14}$aryl$C_{1-8}$alkanyl, di$C_{1-8}$alkanyloxy$C_{6-14}$aryl$C_{1-8}$alkanyl, or $C_{6-14}$aryloxy$C_{6-14}$aryl$C_{1-8}$alkanyl;
(ll) $R^3$ is $C_{1-8}$alkanyl$C_{6-14}$aryl$C_{1-8}$alkanyl, $C_{6-14}$aryl$C_{1-8}$alkanyl, halo$C_{6-14}$aryl$C_{1-8}$alkanyl, $C_{1-8}$alkanyloxy$C_{6-14}$aryl$C_{1-8}$alkanyl, or $C_{6-14}$aryloxy$C_{6-14}$aryl$C_{1-8}$alkanyl;
(mm) $R^3$ is heterocyclic$C_{1-8}$alkanyl, oxoheterocyclic$C_{1-8}$alkanyl, $C_{1-8}$alkanyl$C_{3-8}$cyclicheteroalkanyl$C_{1-8}$alkanyl, $C_{5-14}$heteroaryl, or $C_{1-8}$alkanyl$C_{6-14}$aryl;
(nn) $R^3$ is oxo$C_{3-8}$cyclicheteroalkanyl$C_{1-8}$alkanyl, $C_{1-8}$alkanyl$C_{3-8}$cyclicheteroalkanyl$C_{1-8}$alkanyl, $C_{1-8}$alkanyl, or $C_{3-8}$cyclicheteroalkanyl$C_{1-8}$alkanyl;
(oo) $R^3$ is $C_{1-8}$alkanyl$C_{3-8}$cyclicheteroalkanyl$C_{1-8}$alkanyl, $C_{3-8}$cyclicheteroalkanyl$C_{1-8}$alkanyl, $C_{1-8}$alkanyl, or oxo$C_{3-8}$cyclicheteroalkanyl$C_{1-8}$alkanyl;
(pp) $R^3$ is $C_{1-8}$alkanyl$C_{3-8}$cyclicheteroalkanyl, or $C_{1-8}$alkanyl;
(qq) $R^3$ is $C_{1-8}$alkanyloxy$C_{6-14}$aryl$C_{1-8}$alkanyl, oxo$C_{3-8}$cyclicheteroalkanyl$C_{1-8}$alkanyl, $C_{6-14}$aryl$C_{1-8}$alkanyloxycarbonylaminoalkanyl, $C_{1-8}$alkanyl, $C_{6-14}$aryl$C_{1-8}$alkanyl, $(C_{6-14}$aryl$)(C_{1-8}$alkanylaminocarbonyl$)C_{1-8}$ alkanyl, aminosulfonylC$_{6-14}$arylC$_{1-8}$alkanyl, (C$_{1-8}$alkanylthio)(aminocarbonyl)alkanyl, C$_{1-8}$alkanyl, aminoC$_{1-8}$ alkanyl, C$_{6-14}$arylC$_{1-8}$alkanylheteroalkanyl, C$_{1-8}$alkanylC$_{6-14}$arylaminoC$_{1-8}$alkanyl, C$_{6-14}$aryloxyC$_{1-8}$ alkanyl, or C$_{6-14}$aryloxyC$_{6-14}$aryl;

(rr) combinations of (a) through (qq) above.

Thus, exemplary embodiments of the present invention are as described below.

One embodiment of the present invention is a method of synthesizing a hydroxyethlamino amide of Formula (I) wherein R$^1$ is optionally substituted phenyl;
R$^2$ is C$_{6-14}$arylC$_{1-8}$alkanyl, diC$_{6-14}$arylC$_{1-8}$alkanyl, C$_{1-8}$alkanyl, alkenyl, hydrogen, or N-linked-C$_{1-8}$alkanylcarbonylamino; and
R$^3$ is optionally substituted C$_{1-8}$alkanyl.

Another embodiment of the present invention is a method of synthesizing a hydroxyethlamino amide of Formula (I) wherein R$^1$ is optionally substituted pyridyl and pyrazinyl, quinolyl, or furyl;
R$^2$ is hydrogen, C$_{1-8}$alkanyloxyC$_{6-14}$arylC$_{1-8}$alkanyl, or C$_{1-8}$alkanylC$_{6-14}$arylC$_{1-8}$alkanyl; and
R$^3$ is optionally substituted C$_{1-8}$alkanyl.

Another embodiment of the present invention is a method of synthesizing a hydroxyethlamino amide of Formula (I) wherein R$^1$ is C$_{1-8}$alkanylC$_{6-14}$aryl, C$_{6-14}$arylC$_{1-8}$alkanyl, or diC$_{1-8}$alkanyloxyC$_{6-14}$aryl;
R$^2$ is hydrogen, C$_{1-8}$alkanyl, C$_{5-14}$heteroarylC$_{1-8}$alkanyl, C$_{6-14}$arylC$_{1-8}$alkanyl; and
R$^3$ is heterocyclicC$_{1-8}$alkanyl, oxoheterocyclicC$_{1-8}$alkanyl, C$_{1-8}$alkanylC$_{3-8}$cyclicheteroalkanylC$_{1-8}$alkanyl, C$_{5-14}$heteroaryl, or C$_{1-8}$alkanylC$_{6-14}$aryl.

Another embodiment of the present invention is a method of synthesizing a hydroxyethlamino amide of Formula (I) wherein R$^1$ is C$_{1-8}$alkanylC$_{6-14}$aryl, C$_{6-14}$arylC$_{1-8}$alkanyl, or diC$_{1-8}$alkanyloxyC$_{6-14}$aryl;
R$^2$ is hydrogen, C$_{1-8}$alkanyl, C$_{5-14}$heteroarylC$_{1-8}$alkanyl, C$_{6-14}$arylC$_{1-8}$alkanyl; and
R$^3$ is R$^3$ is C$_{1-8}$alkanylC$_{3-8}$cyclicheteroalkanyl, or C$_{1-8}$alkanyl.

Another embodiment of the present invention is directed to compositions comprising a compound of Formula (I). In on embodiment, such compounds are those of Formula (I) wherein said compound is selected from the group consisting of:

a compound of formula (I) wherein R$^1$ is 4-(phenylmethyl)phenyl, R$^2$ is H, and R$^3$ is 4-methoxyphenylmethyl;

a compound of formula (I) wherein R$^1$ is 4-(phenylmethyl)phenyl, R$^2$ is 3-methylbut-1-yl, and R$^3$ is 4-methoxyphenylmethyl;

a compound of formula (I) wherein R$^1$ is 4-(phenylmethyl)phenyl, R$^2$ is furan-2-yl, and R$^3$ is 4-methoxyphenylmethyl;

a compound of formula (I) wherein R$^1$ is 4-(phenylmethyl)phenyl, R$^2$ is 2-phenyleth-1-yl, and R$^3$ is 3-(1-pyrrolidin-2-one_prop-1yl);

a compound of formula (I) wherein R$^1$ is 4-(phenylmethyl)phenyl, R$^2$ is 3-methylbut-1-yl, and R$^3$ is 3-(1-pyrrolidin-2-one_prop-1 yl);

a compound of formula (I) wherein R$^1$ is 4-(phenylmethyl)phenyl, R$^2$ is 2-phenyleth-1-yl, and R$^3$ is (2-((phenylmethoxycarbonyl)-amino)eth-1-yl);

a compound of formula (I) wherein R$^1$ is 4-(phenylmethyl)phenyl, R$^2$ is 3-methylbut-1-yl, and R$^3$ is (2-((phenylmethoxycarbonyl)-amino)eth-1-yl);

a compound of formula (I) wherein R$^1$ is 3-methoxyphenyl, R$^2$ is 2-phenyleth-1-yl, and R$^3$ is 3-(1-pyrrolidin-2-one_prop-1yl);

a compound of formula (I) wherein R$^1$ is 3-methoxyphenyl, R is 3-methylbut-1-yl, and R$^3$ is 3-(1-pyrrolidin-2-one_prop-1yl);

a compound of formula (I) wherein R$^1$ is 3-methoxyphenyl, R$^2$ is 2-phenyleth-1-yl, and R$^3$ is (2-((phenylmethoxycarbonyl)-amino)eth-1-yl);

a compound of formula (I) wherein R$^1$ is 3-methoxyphenyl, R is 3-methylbut-1-yl, and R$^3$ is (2-((phenylmethoxycarbonyl)-amino)eth-1-yl);

a compound of formula (I) wherein R$^1$ is 3-methylphenyl, R$^2$ is 2-phenyleth-1-yl, and R$^3$ is 3-(1-pyrrolidin-2-one_prop-1yl);

a compound of formula (I) wherein R$^1$ is 3-methylphenyl, R$^2$ is 3-methylbut-1-yl, and R$^3$ is 3-(1-pyrrolidin-2-one_prop-1yl);

a compound of formula (I) wherein R$^1$ is 3-methylphenyl, R$^2$ is 2-phenyleth-1-yl, and R$^3$ is (2-((phenylmethoxycarbonyl)-amino)eth-1-yl);

a compound of formula (I) wherein R$^1$ is 3-methylphenyl, R$^2$ is 3-methylbut-1-yl, and R$^3$ is (2-((phenylmethoxycarbonyl)-amino)eth-1-yl);

a compound of formula (I) wherein R$^1$ is 4-(phenylmethoxy)phenyl, R$^2$ is 2-phenyleth-1-yl, and R$^3$ is 3-(1-pyrrolidin-2-one_prop-1 yl);

a compound of formula (I) wherein R$^1$ is 4-(phenylmethoxy)phenyl, R$^2$ is 3-methylbut-1-yl, and R$^3$ is 3-(1-pyrrolidin-2-one_prop-1yl);

a compound of formula (I) wherein R$^1$ is 4-(phenylmethoxy)phenyl, R$^2$ is 2-phenyleth-1-yl, and R$^3$ is (2-((phenylmethoxycarbonyl)-amino)eth-1-yl);

a compound of formula (I) wherein R$^1$ is 4-(phenylmethoxy)phenyl, R$^2$ is 3-methylbut-1-yl, and R$^3$ is (2-((phenylmethoxycarbonyl)-amino)eth-1-yl);

a compound of formula (I) wherein R$^1$ is 4-(phenylmethyl)phenyl, R$^2$ is 2-phenyleth-1-yl, and R$^3$ is cyclohexyl;

a compound of formula (I) wherein R$^1$ is 4-(phenylmethyl)phenyl, R$^2$ is 3-methylbut-1-yl, and R$^3$ is cyclohexyl;

a compound of formula (I) wherein R$^1$ is 4-(phenylmethyl)phenyl, R$^2$ is 2-phenyleth-1-yl, and R$^3$ is cyclohexylmethyl;

a compound of formula (I) wherein R$^1$ is 4-(phenylmethyl)phenyl, R$^2$ is 3-methylbut-1-yl, and R$^3$ is cyclohexylmethyl;

a compound of formula (I) wherein R$^1$ is 4-(phenylmethyl)phenyl, R$^2$ is 2-phenyleth-1-yl, and R$^3$ is 2-phenyleth-1-yl;

a compound of formula (I) wherein R$^1$ is 4-(phenylmethyl)phenyl, R$^2$ is 3-methylbut-1-yl, and R$^3$ is 2-phenyleth-1-yl;

a compound of formula (I) wherein R$^1$ is 4-(phenylmethyl)phenyl, R$^2$ is 3-methylbut-1-yl, and R$^3$ is 1-(cyclohexylaminocarbonyl)-2-(phenylmethyl);

a compound of formula (I) wherein R$^1$ is 4-(phenylmethyl)phenyl, R$^2$ is 2-phenyleth-1-yl, and R$^3$ is 2-(4-sulfamoylphenyl)eth-1-yl;

a compound of formula (I) wherein R$^1$ is 4-(phenylmethyl)phenyl, R$^2$ is 3-methylbut-1-yl, and R$^3$ is 2-(4-sulfamoylphenyl)eth-1-yl;

a compound of formula (I) wherein R$^1$ is 3-methoxyphenyl, R$^2$ is 3-methylbut-1-yl, and R$^3$ is 4-methylthiobutanamid-2-yl;

a compound of formula (I) wherein R$^1$ is 3-methoxyphenyl, R$^2$ is 2-phenyleth-1-yl, and R$^3$ is cyclohexyl;

a compound of formula (I) wherein $R^1$ is 3-methoxyphenyl, $R^2$ is 3-methylbut-1-yl, and $R^3$ is cyclohexyl;

a compound of formula (I) wherein $R^1$ is 3-methoxyphenyl, $R^2$ is 2-phenyleth-1-yl, and $R^3$ is cyclohexylmethyl;

a compound of formula (I) wherein $R^1$ is 3-methoxyphenyl, $R^2$ is 3-methylbut-1-yl, and $R^3$ is cyclohexylmethyl;

a compound of formula (I) wherein $R^1$ is 3-methoxyphenyl, R is 2-phenyleth-1-yl, and $R^3$ is 2-phenyleth-1-yl;

a compound of formula (I) wherein $R^1$ is 3-methoxyphenyl, $R^2$ is 3-methylbut-1-yl, and $R^3$ is 2-phenyleth-1-yl;

a compound of formula (I) wherein $R^1$ is 3-methoxyphenyl, R is 2-phenyleth-1-yl, and $R^3$ is N-cyclohexyl-3-phenylpropanamide-2-yl;

a compound of formula (I) wherein $R^1$ is 3-methoxyphenyl, R is 3-methylbut-1-yl, and $R^3$ is N-cyclohexyl-3-phenylpropanamide-2-yl;

a compound of formula (I) wherein $R^1$ is 3-methoxyphenyl, R is 2-phenyleth-1-yl, and $R^3$ is 2-(4-sulfamoylphenyl)eth-1-yl;

a compound of formula (I) wherein $R^1$ is 3-methoxyphenyl, R is 3-methylbut-1-yl, and $R^3$ is 2-(4-sulfamoylphenyl)eth-1-yl;

a compound of formula (I) wherein $R^1$ is 3-methoxyphenyl, $R^2$ is 2-phenyleth-1-yl, and $R^3$ is (2-((phenylmethoxycarbonyl)-amino)eth-1-yl);

a compound of formula (I) wherein $R^1$ is 3-methoxyphenyl, R is 3-methylbut-1-yl, and $R^3$ is (2-((phenylmethoxycarbonyl)-amino)eth-1-yl);

a compound of formula (I) wherein $R^1$ is 3-methoxyphenyl, $R^2$ is 2-phenyleth-1-yl, and $R^3$ is 2-aminoeth-1-yl;

a compound of formula (I) wherein $R^1$ is 3-methoxyphenyl, R is 3-methylbut-1-yl, and $R^3$ is 2-aminoeth-1-yl;

a compound of formula (I) wherein $R^1$ is 4-(phenylmethyl)phenyl, $R^2$ is 3-methylbut-1-yl, and $R^3$ is (2-((phenylmethoxycarbonyl)-amino)eth-1-yl);

a compound of formula (I) wherein $R^1$ is 4-(phenylmethyl)phenyl, $R^2$ is 2-phenyleth-1-yl, and $R^3$ is 2-aminoeth-1-yl;

a compound of formula (I) wherein $R^1$ is 4-(phenylmethyl)phenyl, $R^2$ is 3-methylbut-1-yl, and $R^3$ is 2-aminoeth-1-yl;

a compound of formula (I) wherein $R^1$ is 4-methylphenyl, $R^2$ is 3-methylbut-1-yl, and $R^3$ is 2-(4-methylphenyl)eth-1-yl;

a compound of formula (I) wherein $R^1$ is 4-methylphenyl, $R^2$ is 3-methylbut-1-yl, and $R^3$ is 2-phenyleth-1-yl;

a compound of formula (I) wherein $R^1$ is 4-methylphenyl, $R^2$ is 3-methylbut-1-yl, and $R^3$ is 2-(3-fluorophenyl)eth-1-yl;

a compound of formula (I) wherein $R^1$ is 4-methylphenyl, $R^2$ is 3-methylbut-1-yl, and $R^3$ is 2-(3-methoxyphenyl)eth-1-yl;

a compound of formula (I) wherein $R^1$ is 4-methylphenyl, $R^2$ is 3-methylbut-1-yl, and $R^3$ is 2-(3,5-dimethoxyphenyl)eth-1-yl;

a compound of formula (I) wherein $R^1$ is 4-methylphenyl, $R^2$ is 3-methylbut-1-yl, and $R^3$ is 2-(4-phenoxyphenyl)eth-1-yl;

a compound of formula (I) wherein $R^1$ is 4-methylphenyl, $R^2$ is 2-phenyleth-1-yl, and $R^3$ is 2-(4-methylphenyl)eth-1-yl;

a compound of formula (I) wherein $R^1$ is 4-methylphenyl, $R^2$ is 2-phenyleth-1-yl, and $R^3$ is 2-phenyleth-1-yl;

a compound of formula (I) wherein $R^1$ is 4-methylphenyl, $R^2$ is 2-phenyleth-1-yl, and $R^3$ is 2-(3-fluorophenyl)eth-1-yl;

a compound of formula (I) wherein $R^1$ is 4-methylphenyl, $R^2$ is 2-phenyleth-1-yl, and $R^3$ is 2-(3-methoxyphenyl)eth-1-yl;

a compound of formula (I) wherein $R^1$ is 4-methylphenyl, $R^2$ is 2-phenyleth-1-yl, and $R^3$ is 2-(3,5-dimethoxyphenyl)eth-1-yl;

a compound of formula (I) wherein $R^1$ is 4-methylphenyl, $R^2$ is 2-phenyleth-1-yl, and $R^3$ is 2-(4-phenoxyphenyl)eth-1-yl;

a compound of formula (I) wherein $R^1$ is phenylmethyl, $R^2$ is 3-methylbut-1-yl, and $R^3$ is 2-(3-fluorophenyl)eth-1-yl;

a compound of formula (I) wherein $R^1$ is phenylmethyl, $R^2$ is 3-methylbut-1-yl, and $R^3$ is 2-(3-methoxyphenyl)eth-1-yl;

a compound of formula (I) wherein $R^1$ is phenylmethyl, $R^2$ is 3-methylbut-1-yl, and $R^3$ is 2-(3,5-dimethoxyphenyl)eth-1-yl;

a compound of formula (I) wherein $R^1$ is phenylmethyl, $R^2$ is 3-methylbut-1-yl, and $R^3$ is 2-(4-phenoxyphenyl)eth-1-yl;

a compound of formula (I) wherein $R^1$ is phenylmethyl, $R^2$ is 2-phenyleth-1-yl, and $R^3$ is 2-(3-methoxyphenyl)eth-1-yl;

a compound of formula (I) wherein $R^1$ is phenylmethyl, $R^2$ is 2-phenyleth-1-yl, and $R^3$ is 2-(3,5-dimethoxyphenyl)eth-1-yl;

a compound of formula (I) wherein $R^1$ is phenylmethyl, $R^2$ is 2-phenyleth-1-yl, and $R^3$ is 2-(4-phenoxyphenyl)eth-1-yl;

a compound of formula (I) wherein $R^1$ is 3,5-dimethoxyphenyl, $R^2$ is 3-methylbut-1-yl, and $R^3$ is 2-(3,5-dimethoxyphenyl)eth-1-yl;

a compound of formula (I) wherein $R^1$ is 3-(dimethylamino)phenyl, $R^2$ is 3-methylbut-1-yl, and $R^3$ is 2-(3,4-dichlorophenyl)eth-1-yl;

a compound of formula (I) wherein $R^1$ is 3-(dimethylamino)phenyl, $R^2$ is 3-methylbut-1-yl, and $R^3$ is 2-(3-fluorophenyl)eth-1-yl;

a compound of formula (I) wherein $R^1$ is 3-(dimethylamino)phenyl, $R^2$ is 3-methylbut-1-yl, and $R^3$ is 2-(3-methoxyphenyl)eth-1-yl;

a compound of formula (I) wherein $R^1$ is 3-(dimethylamino)phenyl, $R^2$ is 3-methylbut-1-yl, and $R^3$ is 2-(3,5-dimethoxyphenyl)eth-1-yl;

a compound of formula (I) wherein $R^1$ is 3-(dimethylamino)phenyl, $R^2$ is 3-methylbut-1-yl, and $R^3$ is 2-(4-phenoxyphenyl)eth-1-yl;

a compound of formula (I) wherein $R^1$ is 3-(dimethylamino)phenyl, $R^2$ is 2-phenyleth-1-yl, and $R^3$ is 2-(3,4-dichlorophenyl)eth-1-yl;

a compound of formula (I) wherein $R^1$ is 3-(dimethylamino)phenyl, $R^2$ is 2-phenyleth-1-yl, and $R^3$ is 2-(3-fluorophenyl)eth-1-yl;

a compound of formula (I) wherein $R^1$ is 4-acetylphenyl, $R^2$ is 3-methylbut-1-yl, and $R^3$ is 2-(3,4-dichlorophenyl)eth-1-yl;

a compound of formula (I) wherein $R^1$ is 4-acetylphenyl, $R^2$ is 3-methylbut-1-yl, and $R^3$ is 2-phenyleth-1-yl;

a compound of formula (I) wherein $R^1$ is 4-acetylphenyl, $R^2$ is 3-methylbut-1-yl, and $R^3$ is 2-(3-fluorophenyl)eth-1-yl;

a compound of formula (I) wherein $R^1$ is 4-acetylphenyl, $R^2$ is 3-methylbut-1-yl, and $R^3$ is 2-(3-methoxyphenyl)eth-1-yl;

a compound of formula (I) wherein $R^1$ is 4-acetylphenyl, $R^2$ is 3-methylbut-1-yl, and $R^3$ is 2-(4-phenoxyphenyl)eth-1-yl;

a compound of formula (I) wherein $R^1$ is 4-acetylphenyl, $R^2$ is 2-phenyleth-1-yl, and $R^3$ is 2-(3,4-dichlorophenyl)eth-1-yl;

a compound of formula (I) wherein $R^1$ is 4-acetylphenyl, $R^2$ is 2-phenyleth-1-yl, and $R^3$ is 2-phenyleth-1-yl;

a compound of formula (I) wherein $R^1$ is 4-acetylphenyl, $R^2$ is 2-phenyleth-1-yl, and $R^3$ is 2-(3-methoxyphenyl)eth-1-yl;

a compound of formula (I) wherein $R^1$ is 4-acetylphenyl, $R^2$ is 2-phenyleth-1-yl, and $R^3$ is 2-(3,5-dimethoxyphenyl)eth-1-yl;

a compound of formula (I) wherein $R^1$ is 4-acetylphenyl, $R^2$ is 2-phenyleth-1-yl, and $R^3$ is 2-(4-phenoxyphenyl)eth-1-yl;

a compound of formula (I) wherein $R^1$ is 3-trifluoromethylphenyl, $R^2$ is 3-methylbut-1-yl, and $R^3$ is 2-(3,4-dichlorophenyl)eth-1-yl;

a compound of formula (I) wherein $R^1$ is 3-trifluoromethylphenyl, $R^2$ is 3-methylbut-1-yl, and $R^3$ is 2-phenyleth-1-yl;

a compound of formula (I) wherein $R^1$ is 3-trifluoromethylphenyl, $R^2$ is 3-methylbut-1-yl, and $R^3$ is 2-(3-methoxyphenyl)eth-1-yl;

a compound of formula (I) wherein $R^1$ is 3-trifluoromethylphenyl, $R^2$ is 3-methylbut-1-yl, and $R^3$ is 2-(3,5-dimethoxyphenyl)eth-1-yl;

a compound of formula (I) wherein $R^1$ is 2-chloropyrid-4-yl, $R^2$ is 3-methylbut-1-yl, and $R^3$ is 2-(3,4-dichlorophenyl)eth-1-yl;

a compound of formula (I) wherein $R^1$ is 2-chloropyrid-4-yl, $R^2$ is 3-methylbut-1-yl, and $R^3$ is 2-phenyleth-1-yl;

a compound of formula (I) wherein $R^1$ is 2-chloropyrid-4-yl, $R^2$ is 3-methylbut-1-yl, and $R^3$ is 2-(3-fluorophenyl)eth-1-yl;

a compound of formula (I) wherein $R^1$ is 2-chloropyrid-4-yl, $R^2$ is 3-methylbut-1-yl, and $R^3$ is 2-(3-methoxyphenyl)eth-1-yl;

a compound of formula (I) wherein $R^1$ is 2-chloropyrid-4-yl, $R^2$ is 3-methylbut-1-yl, and $R^3$ is 2-(3,5-dimethoxyphenyl)eth-1-yl;

a compound of formula (I) wherein $R^1$ is 2-chloropyrid-4-yl, $R^2$ is 3-methylbut-1-yl, and $R^3$ is 2-(4-ethylphenyl)eth-1-yl;

a compound of formula (I) wherein $R^1$ is 2-chloropyrid-4-yl, $R^2$ is 2-phenyleth-1-yl, and $R^3$ is 2-(3,4-dichlorophenyl)eth-1-yl;

a compound of formula (I) wherein $R^1$ is 2-chloropyrid-4-yl, $R^2$ is 2-phenyleth-1-yl, and $R^3$ is 2-phenyleth-1-yl;

a compound of formula (I) wherein $R^1$ is 2-chloropyrid-4-yl, $R^2$ is 2-phenyleth-1-yl, and $R^3$ is 2-(3-fluorophenyl)eth-1-yl;

a compound of formula (I) wherein $R^1$ is 2-chloropyrid-4-yl, $R^2$ is 2-phenyleth-1-yl, and $R^3$ is 2-(3-methoxyphenyl)eth-1-yl;

a compound of formula (I) wherein $R^1$ is 2-chloropyrid-4-yl, $R^2$ is 2-phenyleth-1-yl, and $R^3$ is 2-(3,5-dimethoxyphenyl)eth-1--yl;

a compound of formula (I) wherein $R^1$ is 2-chloropyrid-4-yl, $R^2$ is 2-phenyleth-1-yl, and $R^3$ is 2-(4-ethylphenyl)eth-1-yl;

a compound of formula (I) wherein $R^1$ is pyrid-3-yl, $R^2$ is 3-methylbut-1-yl, and $R^3$ is 2-(3,4-dichlorophenyl)eth-1-yl;

a compound of formula (I) wherein $R^1$ is pyrid-3-yl, $R^2$ is 3-methylbut-1-yl, and $R^3$ is 2-phenyleth-1-yl;

a compound of formula (I) wherein $R^1$ is pyrid-3-yl, $R^2$ is 3-methylbut-1-yl, and $R^3$ is 2-(3-fluorophenyl)eth-1-yl;

a compound of formula (I) wherein $R^1$ is pyrid-3-yl, $R^2$ is 3-methylbut-1-yl, and $R^3$ is 2-(3,5-dimethoxyphenyl)eth-1-yl;

a compound of formula (I) wherein $R^1$ is pyrid-3-yl, $R^2$ is 3-methylbut-1-yl, and $R^3$ is 2-(4-ethylphenyl)eth-1-yl;

a compound of formula (I) wherein $R^1$ is pyrid-3-yl, $R^2$ is 2-phenyleth-1-yl, and $R^3$ is 2-(3,4-dichlorophenyl)eth-1-yl;

a compound of formula (I) wherein $R^1$ is pyrid-3-yl, $R^2$ is 2-phenyleth-1-yl, and $R^3$ is 2-phenyleth-1-yl;

a compound of formula (I) wherein $R^1$ is pyrid-3-yl, $R^2$ is 2-phenyleth-1-yl, and $R^3$ is 2-(3-fluorophenyl)eth-1-yl;

a compound of formula (I) wherein $R^1$ is pyrid-3-yl, $R^2$ is 2-phenyleth-1-yl, and $R^3$ is 2-(3-methoxyphenyl)eth-1-yl;

a compound of formula (I) wherein $R^1$ is pyrid-3-yl, $R^2$ is 2-phenyleth-1-yl, and $R^3$ is 2-(3,5-dimethoxyphenyl)eth-1-yl;

a compound of formula (I) wherein $R^1$ is pyrid-3-yl, $R^2$ is 2-phenyleth-1-yl, and $R^3$ is 2-(4-ethylphenyl)eth-1-yl;

a compound of formula (I) wherein $R^1$ is pyrazin-2-yl, $R^2$ is 3-methylbut-1-yl, and $R^3$ is 2-(3,4-dichlorophenyl)eth-1-yl;

a compound of formula (I) wherein $R^1$ is pyrazin-2-yl, $R^2$ is 3-methylbut-1-yl, and $R^3$ is 2-phenyleth-1-yl;

a compound of formula (I) wherein $R^1$ is pyrazin-2-yl, $R^2$ is 3-methylbut-1-yl, and $R^3$ is 2-(3-fluorophenyl)eth-1-yl;

a compound of formula (I) wherein $R^1$ is pyrazin-2-yl, $R^2$ is 3-methylbut-1-yl, and $R^3$ is 2-(3-methoxyphenyl)eth-1-yl;

a compound of formula (I) wherein $R^1$ is pyrazin-2-yl, $R^2$ is 3-methylbut-1-yl, and $R^3$ is 2-(3,5-dimethoxyphenyl)eth-1-yl;

a compound of formula (I) wherein $R^1$ is pyrazin-2-yl, $R^2$ is 3-methylbut-1-yl, and $R^3$ is 2-(4-ethylphenyl)eth-1-yl;

a compound of formula (I) wherein $R^1$ is pyrazin-2-yl, $R^2$ is 2-phenyleth-1-yl, and $R^3$ is 2-(3,4-dichlorophenyl)eth-1-yl;

a compound of formula (I) wherein $R^1$ is pyrazin-2-yl, $R^2$ is 2-phenyleth-1-yl, and $R^3$ is 2-phenyleth-1-yl;

a compound of formula (I) wherein $R^1$ is 3-quinolyl, $R^2$ is butyl, and $R^3$ is 2-(morpholin-4-yl)prop-3-yl;

a compound of formula (I) wherein $R^1$ is 3-quinolyl, $R^2$ is butyl, and $R^3$ is 2-(2-pyridyl)eth-1 yl;

a compound of formula (I) wherein $R^1$ is 3-quinolyl, $R^2$ is butyl, and $R^3$ is 2-(2-thienyl)eth-1 yl;

a compound of formula (I) wherein $R^1$ is 3-quinolyl, $R^2$ is butyl, and $R^3$ is 2-(1-pyrrolidin-2-one_eth-1 yl;

a compound of formula (I) wherein $R^1$ is 3-quinolyl, $R^2$ is butyl, and $R^3$ is 2-(2-methyl-1-piperidinyl)eth-1-yl;

a compound of formula (I) wherein $R^1$ is 3-quinolyl, $R^2$ is butyl, and $R^3$ is 2-(4-ethylphenyl)eth-1-yl;

a compound of formula (I) wherein $R^1$ is 3-quinolyl, $R^2$ is 3-methylbut-1-yl, and $R^3$ is 2-(morpholin-4-yl)prop-3-yl;

a compound of formula (I) wherein $R^1$ is 3-quinolyl, $R^2$ is 3-methylbut-1-yl, and $R^3$ is 2-(2-pyridyl)eth-1yl;

a compound of formula (I) wherein $R^1$ is 3-quinolyl, $R^2$ is 3-methylbut-1-yl, and $R^3$ is 2-(2-thienyl)eth-1 yl;

a compound of formula (I) wherein $R^1$ is 3-quinolyl, $R^2$ is 3-methylbut-1-yl, and $R^3$ is 2-(2-methyl-1-piperidinyl)eth-1-yl;

a compound of formula (I) wherein $R^1$ is 3-quinolyl, $R^2$ is 3-methylbut-1-yl, and $R^3$ is 2-(4-ethylphenyl)eth-1-yl;

a compound of formula (I) wherein $R^1$ is cyclohexyl, $R^2$ is butyl, and $R^3$ is 2-(2-pyridyl)eth-1 yl;

a compound of formula (I) wherein $R^1$ is cyclohexyl, $R^2$ is butyl, and $R^3$ is 2-(2-thienyl)eth-1 yl;

a compound of formula (I) wherein $R^1$ is cyclohexyl, $R^2$ is butyl, and $R^3$ is 2-(2-methyl-1-piperidinyl)eth-1-yl;

a compound of formula (I) wherein $R^1$ is cyclohexyl, $R^2$ is butyl, and $R^3$ is 2-(4-ethylphenyl)eth-1-yl;

a compound of formula (I) wherein $R^1$ is cyclohexyl, $R^2$ is 3-methylbut-1-yl, and $R^3$ is 2-(2-pyridyl)eth-1yl;

a compound of formula (I) wherein $R^1$ is cyclohexyl, $R^2$ is 3-methylbut-1-yl, and $R^3$ is 2-(2-thienyl)eth-1yl;

a compound of formula (I) wherein $R^1$ is cyclohexyl, $R^2$ is 3-methylbut-1-yl, and $R^3$ is 2-(1-pyrrolidin-2-one-eth-1yl;

a compound of formula (I) wherein $R^1$ is cyclohexyl, $R^2$ is 3-methylbut-1-yl, and $R^3$ is 2-(2-methyl-1-piperidinyl)eth-1-yl;

a compound of formula (I) wherein $R^1$ is cyclohexyl, $R^2$ is 3-methylbut-1-yl, and $R^3$ is 2-(4-ethylphenyl)eth-1-yl;

a compound of formula (I) wherein $R^1$ is methylthiomethyl, $R^2$ is butyl, and $R^3$ is 2-(morpholin-4-yl)prop-3-yl;

a compound of formula (I) wherein $R^1$ is methylthiomethyl, $R^2$ is butyl, and $R^3$ is 2-(2-pyridyl)eth-1 yl;

a compound of formula (I) wherein $R^1$ is methylthiomethyl, $R^2$ is butyl, and $R^3$ is 2-(2-thienyl)eth-1yl;

a compound of formula (I) wherein $R^1$ is methylthiomethyl, $R^2$ is butyl, and $R^3$ is 2-(1-pyrrolidin-2-one_eth-1 yl;

a compound of formula (I) wherein $R^1$ is methylthiomethyl, $R^2$ is butyl, and $R^3$ is 2-(2-methyl-1-piperidinyl)eth-1-yl;

a compound of formula (I) wherein $R^1$ is methylthiomethyl, $R^2$ is butyl, and $R^3$ is 2-(4-ethylphenyl)eth-1-yl;

a compound of formula (I) wherein $R^1$ is methylthiomethyl, $R^2$ is 3-methylbut-1-yl, and $R^3$ is 2-(morpholin-4-yl)prop-3-yl;

a compound of formula (I) wherein R is methylthiomethyl, $R^2$ is 3-methylbut-1-yl, and $R^3$ is 2-(2-pyridyl)eth-1yl;

a compound of formula (I) wherein $R^1$ is methylthiomethyl, $R^2$ is 3-methylbut-1-yl, and $R^3$ is 2-(2-thienyl)eth-1yl;

a compound of formula (I) wherein $R^1$ is methylthiomethyl, $R^2$ is 3-methylbut-1-yl, and $R^3$ is 2-(2-methyl-1-piperidinyl)eth-1-yl;

a compound of formula (I) wherein $R^1$ is methylthiomethyl, $R^2$ is 3-methylbut-1-yl, and $R^3$ is 2-(4-ethylphenyl)eth-1-yl;

a compound of formula (I) wherein $R^1$ is 3-methylfur-2-yl, $R^2$ is butyl, and $R^3$ is 2-(morpholin-4-yl)prop-3-yl;

a compound of formula (I) wherein $R^1$ is 3-methylfur-2-yl, $R^2$ is butyl, and $R^3$ is 2-(2-pyridyl)eth-1 yl;

a compound of formula (I) wherein $R^1$ is 3-methylfur-2-yl, $R^2$ is butyl, and $R^3$ is 2-(2-thienyl)eth-1 yl;

a compound of formula (I) wherein $R^1$ is 3-methylfur-2-yl, $R^2$ is butyl, and $R^3$ is 2-(1-pyrrolidin-2-one-eth-1 yl;

a compound of formula (I) wherein $R^1$ is 3-methylfur-2-yl, $R^2$ is butyl, and $R^3$ is 2-(2-methyl-1-piperidinyl)eth-1-yl;

a compound of formula (I) wherein $R^1$ is 3-methylfur-2-yl, $R^2$ is butyl, and $R^3$ is 2-(4-ethylphenyl)eth-1-yl;

a compound of formula (I) wherein $R^1$ is 3-methylfur-2-yl, $R^2$ is 3-methylbut-1-yl, and $R^3$ is 2-(morpholin-4-yl)prop-3-yl;

a compound of formula (I) wherein $R^1$ is 3-methylfur-2-yl, $R^2$ is 3-methylbut-1-yl, and $R^3$ is 2-(2-pyridyl)eth-1yl;

a compound of formula (I) wherein $R^1$ is 3-methylfur-2-yl, $R^2$ is 3-methylbut-1-yl, and $R^3$ is 2-(2-thienyl)eth-1yl;

a compound of formula (I) wherein $R^1$ is 3-methylfur-2-yl, $R^2$ is 3-methylbut-1-yl, and $R^3$ is 2-(2-methyl-1-piperidinyl)eth-1-yl;

a compound of formula (I) wherein $R^1$ is 3-methylfur-2-yl, $R^2$ is 3-methylbut-1-yl, and $R^3$ is 2-(4-ethylphenyl)eth-1-yl;

a compound of formula (I) wherein $R^1$ is phenylmethoxy, $R^2$ is 3-methylbut-1-yl, and $R^3$ is 3-benzoxyphenyl;

a compound of formula (I) wherein $R^1$ is phenylmethoxy, $R^2$ is 3-methylbut-1-yl, and $R^3$ is naphth-1-ylmethyl;

a compound of formula (I) wherein $R^1$ is phenylmethoxy, $R^2$ is 2-phenyleth-1-yl, and $R^3$ is naphth-1-ylmethyl;

a compound of formula (I) wherein $R^1$ is phenylmethoxy, $R^2$ is 3-methylbut-1-yl, and $R^3$ is 1-benzylpiperidin-4-yl;

a compound of formula (I) wherein $R^1$ is phenylmethoxy, $R^2$ is 3-methylbut-1-yl, and $R^3$ is 2-(N-(3-methylphenyl)-N-ethylamino)eth-1-yl;

a compound of formula (I) wherein $R^1$ is phenylmethoxy, $R^2$ is 2-phenyleth-1-yl, and $R^3$ is 2-(N-(3-methylphenyl)-N-ethylamino)eth-1-yl;

a compound of formula (I) wherein $R^1$ is phenylmethoxy, $R^2$ is 3-methylbut-1-yl, and $R^3$ is 2-phenoxyeth-1-yl;

a compound of formula (I) wherein $R^1$ is phenylmethoxy, $R^2$ is 2-phenyleth-1-yl, and $R^3$ is 2-phenoxyeth-1-yl;

a compound of formula (I) wherein $R^1$ is acetamidomethyl, $R^2$ is 2-phenyleth-1-yl, and $R^3$ is naphth-1-ylmethyl;

a compound of formula (I) wherein $R^1$ is acetamidomethyl, $R^2$ is 3-methylbut-1-yl, and $R^3$ is 2-(N-(3-methylphenyl)-N-ethylamino)eth-1-yl;

a compound of formula (I) wherein $R^1$ is acetamidomethyl, $R^2$ is 2-phenyleth-1-yl, and $R^3$ is 2-(N-(3-methylphenyl)-N-ethylamino)eth-1-yl;

a compound of formula (I) wherein $R^1$ is phenylmethoxy, $R^2$ is 3-methylbut-1-yl, and $R^3$ is 4-phenoxyphenyl;

a compound of formula (I) wherein $R^1$ is phenylmethoxy, $R^2$ is 2-phenyleth-1-yl, and $R^3$ is 4-phenoxyphenyl;

a compound of formula (I) wherein $R^1$ is phenylmethoxy, $R^2$ is 3-methylbut-1-yl, and $R^3$ is 3-benzoxyphenyl;

a compound of formula (I) wherein $R^1$ is phenylmethoxy, $R^2$ is 2-phenyleth-1-yl, and $R^3$ is 3-benzoxyphenyl;

a compound of formula (I) wherein $R^1$ is phenylmethoxy, $R^2$ is 3-methylbut-1-yl, and $R^3$ is naphth-1-ylmethyl;

a compound of formula (I) wherein $R^1$ is phenylmethoxy, $R^2$ is 2-phenyleth-1-yl, and $R^3$ is naphth-1-ylmethyl;

a compound of formula (I) wherein $R^1$ is phenylmethoxy, $R^2$ is 3-methylbut-1-yl, and $R^3$ is 1-benzylpiperidin-4-yl;

a compound of formula (I) wherein $R^1$ is phenylmethoxy, $R^2$ is 2-phenyleth-1-yl, and $R^3$ is 1-benzylpiperidin-4-yl;

a compound of formula (I) wherein $R^1$ is phenylmethoxy, $R^2$ is 3-methylbut-1-yl, and $R^3$ is 2-(N-(3-methylphenyl)-N-ethylamino)eth-1-yl;

a compound of formula (I) wherein $R^1$ is phenylmethoxy, $R^2$ is 2-phenyleth-1-yl, and $R^3$ is 2-(N-(3-methylphenyl)-N-ethylamino)eth-1-yl;

a compound of formula (I) wherein $R^1$ is phenylmethoxy, $R^2$ is 3-methylbut-1-yl, and $R^3$ is 2-phenoxyeth-1-yl;

a compound of formula (I) wherein $R^1$ is phenylmethoxy, $R^2$ is 2-phenyleth-1-yl, and $R^3$ is 2-phenoxyeth-1-yl;

a compound of formula (I) wherein $R^1$ is pyran-2-one-4-yl, $R^2$ is H, and $R^3$ is 2-(1-pyrrolidin-2-one_eth-1 yl;

a compound of formula (I) wherein $R^1$ is pyran-2-one-4-yl, $R^2$ is H, and $R^3$ is cyclopropylmethyl;

a compound of formula (I) wherein $R^1$ is pyran-2-one-4-yl, $R^2$ is H, and $R^3$ is 2-(2-methyl-1-piperidinyl)eth-1-yl;

a compound of formula (I) wherein $R^1$ is pyran-2-one-4-yl, $R^2$ is H, and $R^3$ is cyclohexylmethyl;

a compound of formula (I) wherein $R^1$ is pyran-2-one-4-yl, $R^2$ is H, and $R^3$ is tetrahydrofuran-2-yl;

a compound of formula (I) wherein $R^1$ is 2-cyclopentyleth-1-yl, $R^2$ is H, and $R^3$ is 2-(morpholin-4-yl)prop-3-yl;

a compound of formula (I) wherein $R^1$ is 2-cyclopentyleth-1-yl, $R^2$ is H, and $R^3$ is 2-(2-methyl-1-piperidinyl)eth-1-yl;

a compound of formula (I) wherein $R^1$ is 2-cyclopentyleth-1-yl, $R^2$ is H, and $R^3$ is cyclohexylmethyl;

a compound of formula (I) wherein $R^1$ is 2-cyclopentyleth-1-yl, $R^2$ is 4-methoxyphenylmethyl, and $R^3$ is tetrahydrofuran-2-yl;

a compound of formula (I) wherein $R^1$ is 2-cyclopentyleth-1-yl, $R^2$ is 4-methoxyphenylmethyl, and $R^3$ is cyclopropylmethyl;

a compound of formula (I) wherein $R^1$ is 2-cyclopentyleth-1-yl, $R^2$ is H, and $R^3$ is tetrahydrofuran-2-yl;

a compound of formula (I) wherein $R^1$ is 2-cyclopentyleth-1-yl, $R^2$ is H, and $R^3$ is cyclopropylmethyl;

a compound of formula (I) wherein $R^1$ is methysulfonylmethyl, $R^2$ is H, and $R^3$ is 3-(2-methyl-1-piperidinyl)prop-1-yl;

a compound of formula (I) wherein $R^1$ is methysulfonylmethyl, $R^2$ is H, and $R^3$ is cyclohexylmethyl;

a compound of formula (I) wherein $R^1$ is 2-phenylethyn-1-yl, $R^2$ is H, and $R^3$ is 2-(morpholin-4-yl)prop-3-yl;

a compound of formula (I) wherein $R^1$ is 2-phenylethyn-1-yl, $R^2$ is H, and $R^3$ is 3-(2-methyl-1-piperidinyl)prop-1-yl;

a compound of formula (I) wherein $R^1$ is 2-phenylethyn-1-yl, $R^2$ is H, and $R^3$ is cyclohexylmethyl;

a compound of formula (I) wherein $R^1$ is 2-phenylethyn-1-yl, $R^2$ is H, and $R^3$ is tetrahydrofuran-2-yl;

a compound of formula (I) wherein $R^1$ is 2-cyclopentyleth-1-yl, $R^2$ is 4-isopropylphenylmethyl, and $R^3$ is 3-(1-pyrrolidin-2-one_prop-1 yl;

a compound of formula (I) wherein $R^1$ is 2-cyclopentyleth-1-yl, $R^2$ is 4-isopropylphenylmethyl, and $R^3$ is 3-(2-methyl-1-piperidinyl)prop-1-yl;

a compound of formula (I) wherein $R^1$ is 2-cyclopentyleth-1-yl, $R^2$ is 4-isopropylphenylmethyl, and $R^3$ is cyclohexylmethyl;

a compound of formula (I) wherein $R^1$ is 2-cyclopentyleth-1-yl, $R^2$ is 4-isopropylphenylmethyl, and $R^3$ is tetrahydrofuran-2-yl;

a compound of formula (I) wherein $R^1$ is 2-cyclopentyleth-1-yl, $R^2$ is 4-isopropylphenylmethyl, and $R^3$ is cyclopropylmethyl;

a compound of formula (I) wherein $R^1$ is 2-phenylethyn-1-yl, $R^2$ is 4-methoxyphenylmethyl, and $R^3$ is cyclohexylmethyl;

a compound of formula (I) wherein $R^1$ is 2-phenylethyn-1-yl, $R^2$ is 4-methoxyphenylmethyl, and $R^3$ is tetrahydrofuran-2-yl; and a compound of formula (I) wherein $R^1$ is 2-phenylethyn-1-yl, $R^2$ is 4-isopropylphenylmethyl, and $R^3$ is 3-(1-pyrrolidin-2-one_prop-1yl;

The present invention is also directed to a compound of formula (Ia):

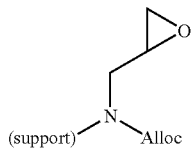

(Ia)

wherein (support) is selected from the group consisting of amine based polystyrene resins. Preferably, (support) is a Rink type resin, and more preferably, (support) is a Rink-AM resin.

The present invention is also directed to a compound of formula (Ib):

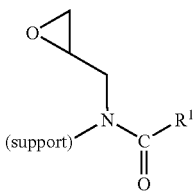

wherein:

$R^1$ is $C_{1-8}$alkanyl, cyclic$C_{1-8}$alkanyl, $C_{6-14}$aryl, $C_{5-14}$heteroaryl $C_{2-8}$alkenyl, $C_{1-8}$alkoxy($C_{2-8}$)alkenyl, $C_{2-8}$alkynyl, $C_{1-8}$alkoxy($C_{2-8}$)alkynyl, heteroaryl($C_{2-8}$)alkenyl, or heteroaryl($C_{2-8}$)alkynyl; wherein said $C_{1-8}$alkanyl, cyclic$C_{1-8}$alkanyl, $C_{6-14}$aryl, $C_{5-14}$heteroaryl $C_{2-8}$alkenyl, $C_{1-8}$alkoxy($C_{2-8}$)alkenyl, $C_{2-8}$alkynyl, $C_{1-8}$alkoxy($C_{2-8}$) alkynyl, heteroaryl($C_{2-8}$)alkenyl, and heteroaryl($C_{2-8}$) alkynyl are optionally substituted with one to two substituents independently selected from the group consisting of $C_{6-14}$aryloxy, di$C_{1-8}$alkanylamino, $C_{1-8}$alkanylamino, $C_{1-8}$alkanyl, $C_{6-14}$aryl, $C_{1-8}$alkanyloxy, $C_{1-8}$alkanylcarbonyl, perhalo$C_{1-6}$alkanyl, halo, $C_{5-14}$heteroaryl, $C_{1-8}$alkanyl, $C_{1-8}$alkanylthio, oxo$C_{5-8}$cyclicheteroalkenyl, $C_{6-14}$arylalkynyl, $C_{1-8}$alkanylsulfonyl, $C_{6-14}$aryl$C_{1-18}$alkanyl, $C_{1-8}$alkanyloxy, $C_{6-14}$aryl$C_{1-8}$alkanyloxy, $C_{6-14}$aryl$C_{1-8}$alkanyloxycarbonylamino, and $C_{1-8}$alkanylcarbonylamino; and wherein (support) is selected from the group consisting of amine based polystyrene resins. Preferably, (support) is a Rink type resin, and more preferably, (support) is a Rink-AM resin.

The compounds of the present invention may also be present in the form of pharmaceutically acceptable salts. For use in medicine, the salts of the compounds of this invention refer to non-toxic "pharmaceutically acceptable salts" (Ref. *International J. Pharm.*, 1986, 33, 201-217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected perenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.01 mg to about 15,000 mg, in particular from about 1 mg to about 5000 mg or, more particularly from about 500 mg to about 4000 mg of active ingredient per day for an average (70 kg) human.

For oral administration, a pharmaceutical composition is preferably provided in the form of tablets containing, 0.01, 10.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics or anti-pyretics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of Formulas (I) and (II) are useful in methods for treating a disease or condition in a mammal characterized by inadequate activity of aspartyl proteases. Such methods comprises administering to a mammal in need of such treatment a therapeutically effective amount of a compound, salt or solvate of Formulas (I) or (II). Such diseases and conditions include Alzheimer's disease and HIV/AIDS.

GENERAL SYNTHETIC METHODS

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

The aminohydroxyalkylamides of formula (I) that comprise this invention are synthesized using the general chemical methods shown in Scheme I.

Abbreviations
Fmoc=9-fluorenylmethoxycarbonyl
DCM=dichloromethane
DCE=dichloroethane

SCHEME 1

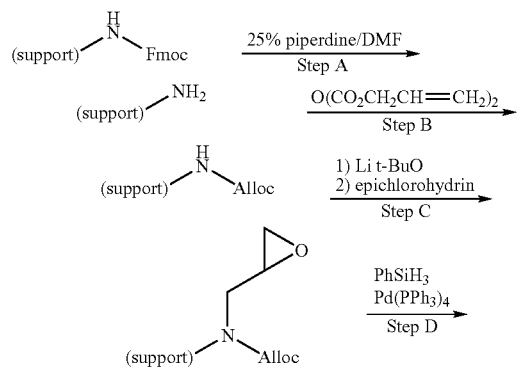

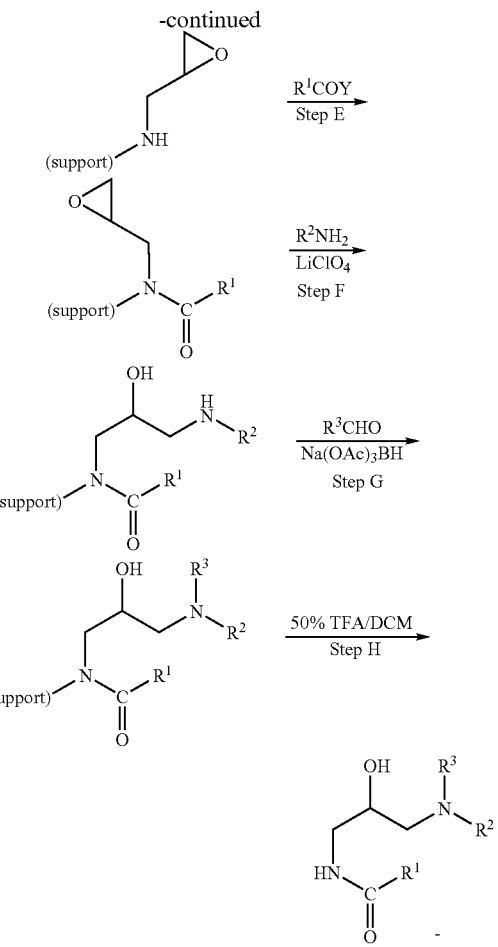

Generation of the Epoxyalkyl Support

Fmoc support is deprotected in a peptide synthesis vessel agitation two times for 1545 min with 25% piperidine/DMF (or other equivalent means, e.g. NMP). Following this agitation, the support is washed successively with DCM then MeOH, followed by DCM. Following deprotection DCM and diisopropylethyl amine are added, followed by 5 equivalent of diallylpyrocarbonate. The mixture is agitated and vented for 12-18-hours. The solution is then drained and the support washed with DCM then MeOH (3 cycles), followed by DCM (3×). The support is then washed with dry THF (or other equivalent solvents, e.g. ethyl ether, dioxane) (2×) and then dry THF (or other equivalent solvents, e.g. ethyl ether, dioxane) is added to the reaction vessel, followed by 10-20 equivalents of Li t-BuO (or other equivalent reagents, e.g. K t-BuO). The mixture is then agitated for 3-6 hours and drained carefully to ensure the support remains wet. 15-30 equivalents of epichlorohydrin in DMSO (or other equivalent solvents, e.g. DMF, DMA, NMP) is then added to the support. The mixture is agitated for 20 hours, the solution is drained, and the support is washed with DCM then MeOH (3 cycles), followed by DCM (3×). The resulting support is then dried under vacuum.

Generation of the Aminohydroxyalkylamides 6-108 equivalents of $PhSiH_3$ in DCE (or other equivalent solvents, e.g. DCM, chloroform) was added to the epoxyalkyl support. The solution is bubbled with nitrogen and then 0.1-1 equivalents of $Pd(PPh_3)_4$ is added. The reaction mixture is bubbled with nitrogen for 2-4 h then the solution is drained and the support washed with DCM then MeOH (3 cycles), followed by DCM (3×). The resulting support is dried under vacuum. The support is then taken up in DCE (or other equivalent solvents, e.g. DCM, chloroform) and 3.5 equivalents of the $R^1$ carboxylic acid or acid derivative ($R^1COY$ where in Y is OH, Cl, Br, $OC_{1-3}$alkanyl or $OOCR^1$) is added in 50% DCE (or other equivalent solvents, e.g. DCM, chloroform)/diisopropylethyl amine, followed by 4.5 equivalents of 2-chloro-1,3-dimethylimidazolidinium chloride in DCM (or other equivalent solvents, e.g. DCM, chloroform). The reaction mixture is agitated for 12-20 hours, the solution is drained, and the support is washed with DCM then MeOH (3 cycles), followed by DCM (3×). To the support from step E was added DCE (or other equivalent solvents, e.g. DCM, chloroform) (2 mL), $R^2NH_2$ and $LiClO_4$ in ethyl ether. The reaction was agitated for 18-22 hours. The solution was drained and the support washed with DCM then MeOH (3 cycles), followed by DCM (3×).

To the support from step F was added DCE (or other equivalent solvents, e.g. DCM, chloroform), $R^3CHO$, trimethyl orthoformate, and $Na(OAc)_3BH$ in DMF (or other equivalent solvents, e.g. NMP). The reaction was agitated for 12-18 hours. The solution was drained and the support was washed with DCM then MeOH (3 cycles), followed by DCM (3×).

Cleaving the Aminohydroxyalkylamides from the Support:

To the support from step G was added 50% TFA/DCM. The support was agitated for 60-120 minutes and the filtrate collected. The support was washed with 2% TFA/DCM (2×). The combined filtrates were concentrated to a residue and purified by reverse-phase chromatography to furnish the product.

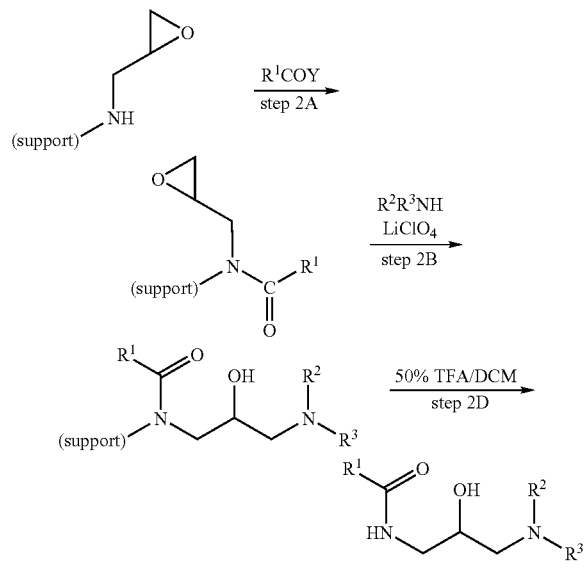

SCHEME 2

The epoxyalkyl support is generated in accordance with the procedures in Scheme 1.

Step 2A:

The support is then taken up in DCE (or other equivalent solvents, e.g. DCM, chloroform) and 3.5 equivalents of the $R^1$ carboxylic acid or acid derivative ($R^1COY$ wherein Y is OH, Cl, Br, $OC_{1-3}$alkanyl or $OOCR^1$) is added in 50% DCE (or other equivalent solvents, e.g. DCM, chloroform)/diisopropylethyl amine, followed by 4.5 equivalents of 2-chloro-1,3-dimethylimidazolidinium chloride in DCM (or other equivalent solvents, e.g. DCM, chloroform). The reaction mixture is agitated for 12-20 hours, the solution is drained, and the support is washed with DCM then MeOH (3 cycles), followed by DCM (3×).

Step 2B:

To the support from step 2A was added DCE (or other equivalent solvents, e.g. DCM, chloroform) (2 mL), $R^2R^3NH$ and $LiClO_4$ in ethyl ether. The reaction was agitated for 18-22 hours. The solution was drained and the support washed with DCM then MeOH (3 cycles), followed by DCM (3×).

Step 2C:

To the support from step 2B was added 50% TFA/DCM. The support was agitated for 60-120 minutes and the filtrate collected. The support was washed with 2% TFA/DCM (2×). The combined filtrates were concentrated to a residue and purified by reverse-phase chromatography to furnish the product.

The structures of the final products are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases where the product is isolated as the acid addition salt the free base may be obtained by techniques known to those skilled in the art. In those cases in which the product is isolated as an acid addition salt, the salt may contain one or more equivalents of the acid.

Representative compounds of the present invention can be synthesized in accordance with the general synthetic methods and schemes described above and are illustrated more particularly below. Since the scheme is an illustration, the invention should not be construed as being limited by the chemical reactions and conditions expressed. The preparation of the various starting materials used in the schemes is well within the skill of persons versed in the art.

EXAMPLE 1

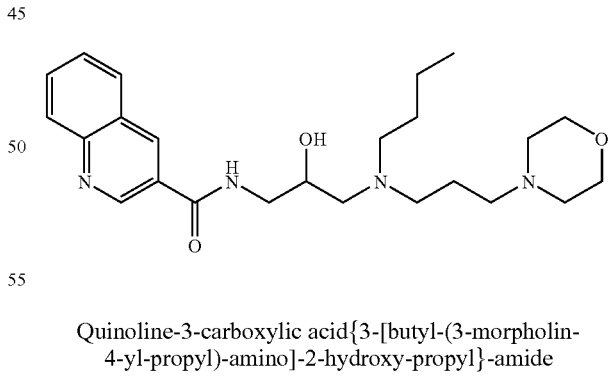

Quinoline-3-carboxylic acid{3-[butyl-(3-morpholin-4-yl-propyl)-amino]-2-hydroxy-propyl}-amide Step A:

To a peptide synthesis vessel was added 25 g Rink-AM resin (Novabiochem 200400 mesh; 0.63 mmol/g loading) and 25% piperidine/DMF (250 mL). The mixture was agitated for 15 min and the solution drained. Once again, 25% piperidine/DMF (250 mL) was added and the mixture was agitated for 30 min. The solution was drained and the resin washed with DCM then MeOH (3 cycles), followed by DCM (3×).

Step B:

To the resin from step A was added DCM (250 mL) and diisopropylethyl amine (10.2 g, 79 mmol), followed by diallylpyrocarbonate (14.7 g, 79 mmol). The mixture was agitated and vented for 18 h. The solution was drained and the resin washed with DCM then MeOH (3 cycles), followed by DCM (3×).

Step C:

The resin from step B was washed with dry THF (2×) and then dry THF (250 mL) was added, followed by Li t-BuO (25.2 g, 0.32 mol). The mixture was agitated for 4 h and then drained carefully to ensure the resin remains wet. To the resin was added DMSO (250 mL) and epichlorohydrin (43.5 g, 0.47 mol). The mixture was agitated for 20 h. The solution was drained and the resin washed with DCM then MeOH (3 cycles), followed by DCM (3×). The resulting resin was dried under vacuum.

Step D:

To the resin (12 g, 7.5 mmol) from step C was added DCE (120 mL) and PhSiH$_3$ (6.5 g, 60 mmol). The solution was bubbled with nitrogen and then Pd(PPh$_3$)$_4$ (1.75 g, 1.51 mmol) was added. The reaction mixture was bubbled with nitrogen for 2 h. The solution was drained and the resin washed with DCM then MeOH (3 cycles), followed by DCM (3×). The resulting resin was dried under vacuum.

Step E:

To a reaction vessel was added resin (200 mg, 0.14 mmol) from step D, DCE (1 mL), and 3-quinolinecarboxylic acid (86 mg, 0.50 mmol) in 50% DCE/diisopropylethyl amine (0.5 mL), followed by 2-chloro-1,3-dimethylimidazolidinium chloride (106 mg, 0.63 mmol) in DCM (0.5 mL). The reaction mixture was agitated for 22 h. The solution was drained and the resin washed with DCM then MeOH (3 cycles), followed by DCM (3×).

Step F:

To the resin from step E was added DCE (2 mL), 4-(3-aminopropyl)morpholine (182 mg, 1.26 mmol), and LiClO$_4$ (13 mg, 0.13 mmol) in ethyl ether (0.1 mL). The reaction was agitated for 22 h. The solution was drained and the resin washed with DCM then MeOH (3 cycles), followed by DCM (3×).

Step G:

To the resin from step F was added DCE (2 mL), butyraldehyde (45 mg, 0.63 mmol), trimethyl orthoformate (0.5 mL), and Na(OAc)$_3$BH (134 mg, 0.63 mmol) in DMF (0.3 mL). The reaction was agitated for 20 h. The solution was drained and the resin was washed with DCM then MeOH (3 cycles), followed by DCM (3×).

Step H:

To the resin from step G was added 50% TFA/DCM (2.5 mL). The resin was agitated for 1 h and the filtrate collected. The resin was washed with 2% TFA/DCM (2×1.5 mL). The combined filtrates were concentrated to a residue and purified by reverse-phase chromatography to furnish the product, quinoline-3-carboxylic acid{3-[butyl-(3-morpholin-4-yl-propyl)-amino]-2-hydroxy-propyl}-amide (33.2 mg, 38.1%) as a trifluoroacetate salt. MS m/z (MH$^+$) calcd 429.2866, found 429.53;

Using the method of Example 1 and appropriately substituted reagents, the following compounds of formula (I) were synthesized:

| R1 | R2 | R3 | Calc'd Mass | Found Mass |
|---|---|---|---|---|
| 4-(phenylmethyl)phenyl | H | 4-methoxyphenylmethyl | 405.2 | 405.3 |
| 4-(phenylmethyl)phenyl | 3-methylbut-1-yl | 4-methoxyphenylmethyl | 475.3 | 475.5 |
| 4-(phenylmethyl)phenyl | furan-2-yl | 4-methoxyphenylmethyl | 485.2 | 485.4 |
| 4-(phenylmethyl)phenyl | 2-phenyleth-1-yl | 3-(1-pyrrolidin-2-one_prop-1yl | 514.3 | 514.4 |
| 4-(phenylmethyl)phenyl | 3-methylbut-1-yl | 3-(1-pyrrolidin-2-one_prop-1yl | 480.3 | 480.5 |
| 4-(phenylmethyl)phenyl | 2-phenyleth-1-yl | (2-((phenylmethoxycarbonyl)-amino)eth-1-yl) | 566.3 | 566.5 |
| 4-(phenylmethyl)phenyl | 3-methylbut-1-yl | (2-((phenylmethoxycarbonyl)-amino)eth-1-yl) | 532.3 | 532.5 |
| 3-methoxyphenyl | 2-phenyleth-1-yl | 3-(1-pyrrolidin-2-one_prop-1yl | 454.3 | 454.4 |
| 3-methoxyphenyl | 3-methylbut-1-yl | 3-(1-pyrrolidin-2-one_prop-1yl | 420.3 | 420.4 |
| 3-methoxyphenyl | 2-phenyleth-1-yl | (2-((phenylmethoxycarbonyl)-amino)eth-1-yl) | 506.3 | 506.4 |
| 3-methoxyphenyl | 3-methylbut-1-yl | (2-((phenylmethoxycarbonyl)-amino)eth-1-yl) | 472.3 | 472.5 |
| 3-methylphenyl | 2-phenyleth-1-yl | 3-(1-pyrrolidin-2-one_prop-1yl | 438.3 | 438.4 |
| 3-methylphenyl | 3-methylbut-1-yl | 3-(1-pyrrolidin-2-one_prop-1yl | 404.3 | 404.4 |
| 3-methylphenyl | 2-phenyleth-1-yl | (2-((phenylmethoxycarbonyl)-amino)eth-1-yl) | 490.3 | 490.4 |
| 3-methylphenyl | 3-methylbut-1-yl | (2-((phenylmethoxycarbonyl)-amino)eth-1-yl) | 456.3 | 456.4 |
| 4-(phenylmethoxy)phenyl | 2-phenyleth-1-yl | 3-(1-pyrrolidin-2-one_prop-1yl | 530.3 | 530.4 |
| 4-(phenylmethoxy)phenyl | 3-methylbut-1-yl | 3-(1-pyrrolidin-2-one_prop-1yl | 496.3 | 496.5 |
| 4-(phenylmethoxy)phenyl | 2-phenyleth-1-yl | (2-((phenylmethoxycarbonyl)-amino)eth-1-yl) | 582.3 | 582.5 |
| 4-(phenylmethoxy)phenyl | 3-methylbut-1-yl | (2-((phenylmethoxycarbonyl)-amino)eth-1-yl) | 548.3 | 548.5 |
| 4-(phenylmethyl)phenyl | 2-phenyleth-1-yl | cyclohexyl | 471.3 | 471.6 |
| 4-(phenylmethyl)phenyl | 3-methylbut-1-yl | cyclohexyl | 437.3 | 437.5 |
| 4-(phenylmethyl)phenyl | 2-phenyleth-1-yl | cyclohexylmethyl | 485.3 | 485.6 |
| 4-(phenylmethyl)phenyl | 3-methylbut-1-yl | cyclohexylmethyl | 451.3 | 451.6 |
| 4-(phenylmethyl)phenyl | 2-phenyleth-1-yl | 2-phenyleth-1-yl | 493.3 | 493.5 |
| 4-(phenylmethyl)phenyl | 3-methylbut-1-yl | 2-phenyleth-1-yl | 459.3 | 459.6 |
| 4-(phenylmethyl)phenyl | 3-methylbut-1-yl | 1-(cyclohexylaminocarbonyl)-2-(phenylmethyl) | 584.4 | 584.7 |
| 4-(phenylmethyl)phenyl | 2-phenyleth-1-yl | 2-(4-sulfamoylphenyl)eth-1-yl | 572.3 | 572.6 |
| 4-(phenylmethyl)phenyl | 3-methylbut-1-yl | 2-(4-sulfamoylphenyl)eth-1-yl | 538.3 | 538.5 |
| 3-methoxyphenyl | 3-methylbut-1-yl | 4-methylthiobutanamid-2-yl | 426.2 | 426.4 |
| 3-methoxyphenyl | 2-phenyleth-1-yl | cyclohexyl | 411.3 | 411.5 |
| 3-methoxyphenyl | 3-methylbut-1-yl | cyclohexyl | 377.3 | 377.5 |
| 3-methoxyphenyl | 2-phenyleth-1-yl | cyclohexylmethyl | 425.3 | 425.5 |
| 3-methoxyphenyl | 3-methylbut-1-yl | cyclohexylmethyl | 391.3 | 391.5 |
| 3-methoxyphenyl | 2-phenyleth-1-yl | 2-phenyleth-1-yl | 433.3 | 433.5 |
| 3-methoxyphenyl | 3-methylbut-1-yl | 2-phenyleth-1-yl | 399.3 | 399.5 |
| 3-methoxyphenyl | 2-phenyleth-1-yl | N-cyclohexyl-3-phenylpropanamide-2-yl | 558.3 | 558.6 |
| 3-methoxyphenyl | 3-methylbut-1-yl | N-cyclohexyl-3-phenylpropanamide-2-yl | 524.4 | 524.6 |

-continued

| R1 | R2 | R3 | Calc'd Mass | Found Mass |
|---|---|---|---|---|
| 3-methoxyphenyl | 2-phenyleth-1-yl | 2-(4-sulfamoylphenyl)eth-1-yl | 512.2 | 512.4 |
| 3-methoxyphenyl | 3-methylbut-1-yl | 2-(4-sulfamoylphenyl)eth-1-yl | 478.2 | 478.5 |
| 3-methoxyphenyl | 2-phenyleth-1-yl | (2-((phenylmethoxycarbonyl)-amino)eth-1-yl) | 520.3 | 520.5 |
| 3-methoxyphenyl | 3-methylbut-1-yl | (2-((phenylmethoxycarbonyl)-amino)eth-1-yl) | 486.3 | 486.5 |
| 3-methoxyphenyl | 2-phenyleth-1-yl | 2-aminoeth-1-yl | 372.2 | 372.5 |
| 3-methoxyphenyl | 3-methylbut-1-yl | 2-aminoeth-1-yl | 338.2 | 338.4 |
| 4-(phenylmethyl)phenyl | 3-methylbut-1-yl | (2-((phenylmethoxycarbonyl)-amino)eth-1-yl) | 546.3 | 546.6 |
| 4-(phenylmethyl)phenyl | 2-phenyleth-1-yl | 2-aminoeth-1-yl | 432.3 | 432.4 |
| 4-(phenylmethyl)phenyl | 3-methylbut-1-yl | 2-aminoeth-1-yl | 398.3 | 398.5 |
| 4-methylphenyl | 3-methylbut-1-yl | 2-(4-methylphenyl)eth-1-yl | 397.3 | 397.5 |
| 4-methylphenyl | 3-methylbut-1-yl | 2-phenyleth-1-yl | 383.3 | 383.5 |
| 4-methylphenyl | 3-methylbut-1-yl | 2-(3-fluorophenyl)eth-1-yl | 401.3 | 401.4 |
| 4-methylphenyl | 3-methylbut-1-yl | 2-(3-methoxyphenyl)eth-1-yl | 413.3 | 413.5 |
| 4-methylphenyl | 3-methylbut-1-yl | 2-(3,5-dimethoxyphenyl)eth-1-yl | 443.3 | 443.5 |
| 4-methylphenyl | 3-methylbut-1-yl | 2-(4-phenoxyphenyl)eth-1-yl | 475.3 | 475.5 |
| 4-methylphenyl | 2-phenyleth-1-yl | 2-(4-methylphenyl)eth-1-yl | 431.3 | 431.5 |
| 4-methylphenyl | 2-phenyleth-1-yl | 2-phenyleth-1-yl | 417.3 | 417.4 |
| 4-methylphenyl | 2-phenyleth-1-yl | 2-(3-fluorophenyl)eth-1-yl | 435.2 | 435.5 |
| 4-methylphenyl | 2-phenyleth-1-yl | 2-(3-methoxyphenyl)eth-1-yl | 447.3 | 447.5 |
| 4-methylphenyl | 2-phenyleth-1-yl | 2-(3,5-dimethoxyphenyl)eth-1-yl | 477.3 | 477.5 |
| 4-methylphenyl | 2-phenyleth-1-yl | 2-(4-phenoxyphenyl)eth-1-yl | 509.3 | 509.5 |
| phenylmethyl | 3-methylbut-1-yl | 2-(3-fluorophenyl)eth-1-yl | 401.3 | 401.5 |
| phenylmethyl | 3-methylbut-1-yl | 2-(3-methoxyphenyl)eth-1-yl | 413.3 | 413.5 |
| phenylmethyl | 3-methylbut-1-yl | 2-(3,5-dimethoxyphenyl)eth-1-yl | 443.3 | 443.5 |
| phenylmethyl | 3-methylbut-1-yl | 2-(4-phenoxyphenyl)eth-1-yl | 475.3 | 475.5 |
| phenylmethyl | 2-phenyleth-1-yl | 2-(3-methoxyphenyl)eth-1-yl | 447.3 | 447.5 |
| phenylmethyl | 2-phenyleth-1-yl | 2-(3,5-dimethoxyphenyl)eth-1-yl | 477.3 | 477.5 |
| phenylmethyl | 2-phenyleth-1-yl | 2-(4-phenoxyphenyl)eth-1-yl | 509.3 | 509.5 |
| 3,5-dimethoxyphenyl | 3-methylbut-1-yl | 2-(3,5-dimethoxyphenyl)eth-1-yl | 489.3 | 489.6 |
| 3-(dimethylamino)phenyl | 3-methylbut-1-yl | 2-(3,4-dichlorophenyl)eth-1-yl | 480.2 | 480.6 |
| 3-(dimethylamino)phenyl | 3-methylbut-1-yl | 2-(3-fluorophenyl)eth-1-yl | 430.3 | 430.6 |
| 3-(dimethylamino)phenyl | 3-methylbut-1-yl | 2-(3-methoxyphenyl)eth-1-yl | 442.3 | 442.6 |
| 3-(dimethylamino)phenyl | 3-methylbut-1-yl | 2-(3,5-dimethoxyphenyl)eth-1-yl | 472.3 | 472.5 |
| 3-(dimethylamino)phenyl | 3-methylbut-1-yl | 2-(4-phenoxyphenyl)eth-1-yl | 504.3 | 504.6 |
| 3-(dimethylamino)phenyl | 2-phenyleth-1-yl | 2-(3,4-dichlorophenyl)eth-1-yl | 514.2 | 514.5 |
| 3-(dimethylamino)phenyl | 2-phenyleth-1-yl | 2-(3-fluorophenyl)eth-1-yl | 464.3 | 464.6 |
| 4-acetylphenyl | 3-methylbut-1-yl | 2-(3,4-dichlorophenyl)eth-1-yl | 479.2 | 479.5 |
| 4-acetylphenyl | 3-methylbut-1-yl | 2-phenyleth-1-yl | 411.3 | 411.5 |
| 4-acetylphenyl | 3-methylbut-1-yl | 2-(3-fluorophenyl)eth-1-yl | 429.3 | 429.5 |
| 4-acetylphenyl | 3-methylbut-1-yl | 2-(3-methoxyphenyl)eth-1-yl | 441.3 | 441.6 |
| 4-acetylphenyl | 3-methylbut-1-yl | 2-(4-phenoxyphenyl)eth-1-yl | 503.3 | 503.6 |
| 4-acetylphenyl | 2-phenyleth-1-yl | 2-(3,4-dichlorophenyl)eth-1-yl | 513.2 | 513.5 |
| 4-acetylphenyl | 2-phenyleth-1-yl | 2-phenyleth-1-yl | 445.3 | 445.6 |
| 4-acetylphenyl | 2-phenyleth-1-yl | 2-(3-methoxyphenyl)eth-1-yl | 475.3 | 475.6 |
| 4-acetylphenyl | 2-phenyleth-1-yl | 2-(3,5-dimethoxyphenyl)eth-1-yl | 505.3 | 505.6 |
| 4-acetylphenyl | 2-phenyleth-1-yl | 2-(4-phenoxyphenyl)eth-1-yl | 537.3 | 537.7 |
| 3-trifluoromethylphenyl | 3-methylbut-1-yl | 2-(3,4-dichlorophenyl)eth-1-yl | 505.2 | 505.4 |
| 3-trifluoromethylphenyl | 3-methylbut-1-yl | 2-phenyleth-1-yl | 437.2 | 437.5 |
| 3-trifluoromethylphenyl | 3-methylbut-1-yl | 2-(3-methoxyphenyl)eth-1-yl | 467.3 | 467.6 |
| 3-trifluoromethylphenyl | 3-methylbut-1-yl | 2-(3,5-dimethoxyphenyl)eth-1-yl | 497.3 | 497.6 |
| 2-chloropyrid-4-yl | 3-methylbut-1-yl | 2-(3,4-dichlorophenyl)eth-1-yl | 472.1 | 472.5 |
| 2-chloropyrid-4-yl | 3-methylbut-1-yl | 2-phenyleth-1-yl | 404.2 | 404.5 |
| 2-chloropyrid-4-yl | 3-methylbut-1-yl | 2-(3-fluorophenyl)eth-1-yl | 422.2 | 422.5 |
| 2-chloropyrid-4-yl | 3-methylbut-1-yl | 2-(3-methoxyphenyl)eth-1-yl | 434.2 | 434.5 |
| 2-chloropyrid-4-yl | 3-methylbut-1-yl | 2-(3,5-dimethoxyphenyl)eth-1-yl | 464.2 | 464.6 |
| 2-chloropyrid-4-yl | 3-methylbut-1-yl | 2-(4-ethylphenyl)eth-1-yl | 432.2 | 432.5 |
| 2-chloropyrid-4-yl | 2-phenyleth-1-yl | 2-(3,4-dichlorophenyl)eth-1-yl | 506.1 | 506.4 |
| 2-chloropyrid-4-yl | 2-phenyleth-1-yl | 2-phenyleth-1-yl | 438.2 | 438.5 |
| 2-chloropyrid-4-yl | 2-phenyleth-1-yl | 2-(3-fluorophenyl)eth-1-yl | 456.2 | 456.5 |
| 2-chloropyrid-4-yl | 2-phenyleth-1-yl | 2-(3-methoxyphenyl)eth-1-yl | 468.2 | 468.6 |
| 2-chloropyrid-4-yl | 2-phenyleth-1-yl | 2-(3,5-dimethoxyphenyl)eth-1-yl | 498.2 | 498.5 |
| 2-chloropyrid-4-yl | 2-phenyleth-1-yl | 2-(4-ethylphenyl)eth-1-yl | 466.2 | 466.6 |
| pyrid-3-yl | 3-methylbut-1-yl | 2-(3,4-dichlorophenyl)eth-1-yl | 438.2 | 438.5 |
| pyrid-3-yl | 3-methylbut-1-yl | 2-phenyleth-1-yl | 370.3 | 370.5 |
| pyrid-3-yl | 3-methylbut-1-yl | 2-(3-fluorophenyl)eth-1-yl | 388.2 | 388.5 |
| pyrid-3-yl | 3-methylbut-1-yl | 2-(3,5-dimethoxyphenyl)eth-1-yl | 430.3 | 430.5 |
| pyrid-3-yl | 3-methylbut-1-yl | 2-(4-ethylphenyl)eth-1-yl | 398.3 | 398.6 |
| pyrid-3-yl | 2-phenyleth-1-yl | 2-(3,4-dichlorophenyl)eth-1-yl | 472.2 | 472.5 |
| pyrid-3-yl | 2-phenyleth-1-yl | 2-phenyleth-1-yl | 404.2 | 404.5 |
| pyrid-3-yl | 2-phenyleth-1-yl | 2-(3-fluorophenyl)eth-1-yl | 422.2 | 422.5 |
| pyrid-3-yl | 2-phenyleth-1-yl | 2-(3-methoxyphenyl)eth-1-yl | 434.2 | 434.5 |
| pyrid-3-yl | 2-phenyleth-1-yl | 2-(3,5-dimethoxyphenyl)eth-1-yl | 464.3 | 464.6 |
| pyrid-3-yl | 2-phenyleth-1-yl | 2-(4-ethylphenyl)eth-1-yl | 432.3 | 432.5 |
| pyrazin-2-yl | 3-methylbut-1-yl | 2-(3,4-dichlorophenyl)eth-1-yl | 439.2 | 439.4 |
| pyrazin-2-yl | 3-methylbut-1-yl | 2-phenyleth-1-yl | 371.2 | 371.5 |
| pyrazin-2-yl | 3-methylbut-1-yl | 2-(3-fluorophenyl)eth-1-yl | 389.2 | 389.5 |
| pyrazin-2-yl | 3-methylbut-1-yl | 2-(3-methoxyphenyl)eth-1-yl | 401.3 | 401.5 |

-continued

| R1 | R2 | R3 | Calc'd Mass | Found Mass |
|---|---|---|---|---|
| pyrazin-2-yl | 3-methylbut-1-yl | 2-(3,5-dimethoxyphenyl)eth-1-yl | 431.3 | 431.5 |
| pyrazin-2-yl | 3-methylbut-1-yl | 2-(4-ethylphenyl)eth-1-yl | 399.3 | 399.5 |
| pyrazin-2-yl | 2-phenyleth-1-yl | 2-(3,4-dichlorophenyl)eth-1-yl | 473.2 | 473.5 |
| pyrazin-2-yl | 2-phenyleth-1-yl | 2-phenyleth-1-yl | 405.2 | 405.5 |
| 3-quinolyl | butyl | 2-(morpholin-4-yl)prop-3-yl | 429.3 | 429.5 |
| 3-quinolyl | butyl | 2-(2-pyridyl)eth-1yl | 407.2 | 407.5 |
| 3-quinolyl | butyl | 2-(2-thienyl)eth-1yl | 412.2 | 412.4 |
| 3-quinolyl | butyl | 2-(1-pyrrolidin-2-one__eth-1yl | 427.3 | 427.5 |
| 3-quinolyl | butyl | 2-(2-methyl-1-piperidinyl)eth-1-yl | 441.3 | 441.6 |
| 3-quinolyl | butyl | 2-(4-ethylphenyl)eth-1-yl | 434.3 | 434.5 |
| 3-quinolyl | 3-methylbut-1-yl | 2-(morpholin-4-yl)prop-3-yl | 443.3 | 443.6 |
| 3-quinolyl | 3-methylbut-1-yl | 2-(2-pyridyl)eth-1-yl | 421.3 | 421.5 |
| 3-quinolyl | 3-methylbut-1-yl | 2-(2-thienyl)eth-1-yl | 426.2 | 426.5 |
| 3-quinolyl | 3-methylbut-1-yl | 2-(2-methyl-1-piperidinyl)eth-1-yl | 455.3 | 455.7 |
| 3-quinolyl | 3-methylbut-1-yl | 2-(4-ethylphenyl)eth-1-yl | 448.3 | 448.6 |
| cyclohexyl | butyl | 2-(2-pyridyl)eth-1-yl | 362.3 | 362.5 |
| cyclohexyl | butyl | 2-(2-thienyl)eth-1-yl | 367.2 | 367.5 |
| cyclohexyl | butyl | 2-(2-methyl-1-piperidinyl)eth-1-yl | 396.4 | 396.4 |
| cyclohexyl | butyl | 2-(4-ethylphenyl)eth-1-yl | 389.3 | 389.6 |
| cyclohexyl | 3-methylbut-1-yl | 2-(2-pyridyl)eth-1-yl | 376.3 | 376.6 |
| cyclohexyl | 3-methylbut-1-yl | 2-(2-thienyl)eth-1-yl | 381.3 | 381.5 |
| cyclohexyl | 3-methylbut-1-yl | 2-(1-pyrrolidin-2-one__eth-1-yl | 396.3 | 396.3 |
| cyclohexyl | 3-methylbut-1-yl | 2-(2-methyl-1-piperidinyl)eth-1-yl | 410.4 | 410.4 |
| cyclohexyl | 3-methylbut-1-yl | 2-(4-ethylphenyl)eth-1-yl | 403.3 | 403.6 |
| methylthiomethyl | butyl | 2-(morpholin-4-yl)prop-3-yl | 362.3 | 362.2 |
| methylthiomethyl | butyl | 2-(2-pyridyl)eth-1yl | 340.2 | 340.2 |
| methylthiomethyl | butyl | 2-(2-thienyl)eth-1yl | 345.2 | 345.4 |
| methylthiomethyl | butyl | 2-(1-pyrrolidin-2-one__eth-1yl | 360.2 | 360.5 |
| methylthiomethyl | butyl | 2-(2-methyl-1-piperidinyl)eth-1-yl | 374.3 | 374.5 |
| methylthiomethyl | butyl | 2-(4-ethylphenyl)eth-1-yl | 367.2 | 367.5 |
| methylthiomethyl | 3-methylbut-1-yl | 2-(morpholin-4-yl)prop-3-yl | 376.3 | 376.5 |
| methylthiomethyl | 3-methylbut-1-yl | 2-(2-pyridyl)eth-1-yl | 354.2 | 354.5 |
| methylthiomethyl | 3-methylbut-1-yl | 2-(2-thienyl)eth-1-yl | 359.2 | 359.4 |
| methylthiomethyl | 3-methylbut-1-yl | 2-(2-methyl-1-piperidinyl)eth-1-yl | 388.3 | 388.5 |
| methylthiomethyl | 3-methylbut-1-yl | 2-(4-ethylphenyl)eth-1-yl | 381.3 | 381.5 |
| 3-methylfur-2-yl | butyl | 2-(morpholin-4-yl)prop-3-yl | 382.3 | 382.6 |
| 3-methylfur-2-yl | butyl | 2-(2-pyridyl)eth-1-yl | 360.2 | 360.5 |
| 3-methylfur-2-yl | butyl | 2-(2-thienyl)eth-1-yl | 365.2 | 365.5 |
| 3-methylfur-2-yl | butyl | 2-(1-pyrrolidin-2-one__eth-1yl | 380.3 | 380.5 |
| 3-methylfur-2-yl | butyl | 2-(2-methyl-1-piperidinyl)eth-1-yl | 394.3 | 394.6 |
| 3-methylfur-2-yl | butyl | 2-(4-ethylphenyl)eth-1-yl | 387.3 | 387.5 |
| 3-methylfur-2-yl | 3-methylbut-1-yl | 2-(morpholin-4-yl)prop-3-yl | 396.3 | 396.6 |
| 3-methylfur-2-yl | 3-methylbut-1-yl | 2-(2-pyridyl)eth-1-yl | 374.2 | 374.5 |
| 3-methylfur-2-yl | 3-methylbut-1-yl | 2-(2-thienyl)eth-1-yl | 379.2 | 379.5 |
| 3-methylfur-2-yl | 3-methylbut-1-yl | 2-(2-methyl-1-piperidinyl)eth-1-yl | 408.3 | 408.6 |
| 3-methylfur-2-yl | 3-methylbut-1-yl | 2-(4-ethylphenyl)eth-1-yl | 401.3 | 401.5 |
| phenylmethoxy | 3-methylbut-1-yl | 3-benzoxyphenyl | 534.3 | 534.6 |
| phenylmethoxy | 3-methylbut-1-yl | naphth-1-ylmethyl | 492.3 | 492.6 |
| phenylmethoxy | 2-phenyleth-1-yl | naphth-1-ylmethyl | 526.3 | 526.5 |
| phenylmethoxy | 3-methylbut-1-yl | 1-benzylpiperidin-4-yl | 525.3 | 525.6 |
| phenylmethoxy | 3-methylbut-1-yl | 2-(N-(3-methylphenyl)-N-ethylamino)eth-1-yl | 513.3 | 513.6 |
| phenylmethoxy | 2-phenyleth-1-yl | 2-(N-(3-methylphenyl)-N-ethylamino)eth-1-yl | 547.3 | 547.6 |
| phenylmethoxy | 3-methylbut-1-yl | 2-phenoxyeth-1-yl | 472.3 | 472.6 |
| phenylmethoxy | 2-phenyleth-1-yl | 2-phenoxyeth-1-yl | 506.3 | 506.5 |
| acetamidomethyl | 2-phenyleth-1-yl | naphth-1-ylmethyl | 434.2 | 434.5 |
| acetamidomethyl | 3-methylbut-1-yl | 2-(N-(3-methylphenyl)-N-ethylamino)eth-1-yl | 421.3 | 421.5 |
| acetamidomethyl | 2-phenyleth-1-yl | 2-(N-(3-methylphenyl)-N-ethylamino)eth-1-yl | 455.3 | 455.6 |
| phenylmethoxy | 3-methylbut-1-yl | 4-phenoxyphenyl | 534.3 | 534.6 |
| phenylmethoxy | 2-phenyleth-1-yl | 4-phenoxyphenyl | 568.3 | 568.6 |
| phenylmethoxy | 3-methylbut-1-yl | 3-benzoxyphenyl | 548.3 | 548.6 |
| phenylmethoxy | 2-phenyleth-1-yl | 3-benzoxyphenyl | 582.3 | 582.6 |
| phenylmethoxy | 3-methylbut-1-yl | naphth-1-ylmethyl | 506.3 | 506.5 |
| phenylmethoxy | 2-phenyleth-1-yl | naphth-1-ylmethyl | 540.3 | 540.6 |
| phenylmethoxy | 3-methylbut-1-yl | 1-benzylpiperidin-4-yl | 539.4 | 539.6 |
| phenylmethoxy | 2-phenyleth-1-yl | 1-benzylpiperidin-4-yl | 573.3 | 573.7 |
| phenylmethoxy | 3-methylbut-1-yl | 2-(N-(3-methylphenyl)-N-ethylamino)eth-1-yl | 527.4 | 527.6 |
| phenylmethoxy | 2-phenyleth-1-yl | 2-(N-(3-methylphenyl)-N-ethylamino)eth-1-yl | 561.3 | 561.7 |
| phenylmethoxy | 3-methylbut-1-yl | 2-phenoxyeth-1-yl | 486.3 | 486.6 |
| phenylmethoxy | 2-phenyleth-1-yl | 2-phenoxyeth-1-yl | 520.3 | 520.5 |
| pyran-2-one-4-yl | H | 2-(1-pyrrolidin-2-one__eth-1yl | 338.2 | 338.5 |
| pyran-2-one-4-yl | H | cyclopropylmethyl | 267.1 | 267.5 |
| pyran-2-one-4-yl | H | 2-(2-methyl-1-piperidinyl)eth-1-yl | 352.2 | 352.6 |
| pyran-2-one-4-yl | H | cyclohexylmethyl | 309.2 | |
| pyran-2-one-4-yl | H | tetrahydrofuran-2-yl | 297.2 | 297.5 |
| 2-cyclopentyleth-1-yl | H | 2-(morpholin-4-yl)prop-3-yl | 342.3 | 342.6 |
| 2-cyclopentyleth-1-yl | H | 2-(2-methyl-1-piperidinyl)eth-1-yl | 354.3 | 354.7 |
| 2-cyclopentyleth-1-yl | H | cyclohexylmethyl | 311.3 | 311.6 |

-continued

| R1 | R2 | R3 | Calc'd Mass | Found Mass |
|---|---|---|---|---|
| 2-cyclopentyleth-1-yl | 4-methoxyphenylmethyl | tetrahydrofuran-2-yl | 419.3 | 419.7 |
| 2-cyclopentyleth-1-yl | 4-methoxyphenylmethyl | cyclopropylmethyl | 389.3 | 389.7 |
| 2-cyclopentyleth-1-yl | H | tetrahydrofuran-2-yl | 299.2 | 299.6 |
| 2-cyclopentyleth-1-yl | H | cyclopropylmethyl | 269.2 | 269.5 |
| methysulfonylmethyl | H | 3-(2-methyl-1-piperidinyl)prop-1-yl | 350.2 | 349.6 |
| methysulfonylmethyl | H | cyclohexylmethyl | 307.2 | 307.5 |
| 2-phenylethyn-1-yl | H | 2-(morpholin-4-yl)prop-3-yl | 346.2 | 346.6 |
| 2-phenylethyn-1-yl | H | 3-(2-methyl-1-piperidinyl)prop-1-yl | 358.3 | 358.6 |
| 2-phenylethyn-1-yl | H | cyclohexylmethyl | 315.2 | 315.5 |
| 2-phenylethyn-1-yl | H | tetrahydrofuran-2-yl | 303.2 | 303.5 |
| 2-cyclopentyleth-1-yl | 4-isopropylphenylmethyl | 3-(1-pyrrolidin-2-one__prop-1yl | 472.4 | 472.8 |
| 2-cyclopentyleth-1-yl | 4-isopropylphenylmethyl | 3-(2-methyl-1-piperidinyl)prop-1-yl | 486.4 | 486.9 |
| 2-cyclopentyleth-1-yl | 4-isopropylphenylmethyl | cyclohexylmethyl | 443.4 | 443.8 |
| 2-cyclopentyleth-1-yl | 4-isopropylphenylmethyl | tetrahydrofuran-2-yl | 431.3 | 431.7 |
| 2-cyclopentyleth-1-yl | 4-isopropylphenylmethyl | cyclopropylmethyl | 401.3 | 401.7 |
| 2-phenylethyn-1-yl | 4-methoxyphenylmethyl | cyclohexylmethyl | 435.3 | 435.7 |
| 2-phenylethyn-1-yl | 4-methoxyphenylmethyl | tetrahydrofuran-2-yl | 423.2 | 423.6 |
| 2-phenylethyn-1-yl | 4-isopropylphenylmethyl | 3-(1-pyrrolidin-2-one__prop-1yl | 476.3 | 476.8 |

EXAMPLE 2

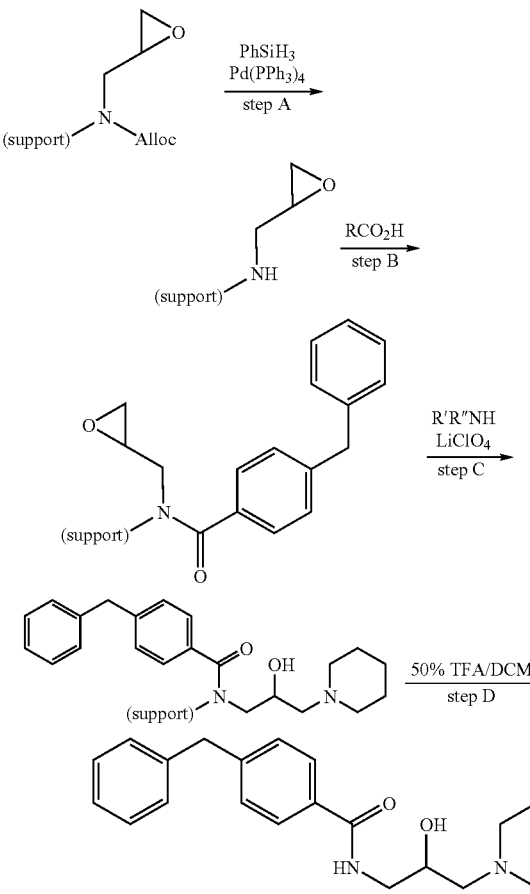

Step A:

To the Alloc-Rink AM resin (200 mg, 0.13 mmol) was added DCE (2 mL) and PhSiH$_3$ (130 uL, 1.04 mmol). The solution was bubbled with nitrogen and then Pd(PPh$_3$)$_4$ (30 mg, 0.02 mmol) was added. The reaction mixture was bubbled with nitrogen for 2 h. The solution was drained and the resin washed with DCM then MeOH (3 cycles), followed by DCM (3×).

Step B:

To the resin from step A was added DCE (2 mL), diisopropylethylamine (0.25 mL), diphenylmethane-4-carboxylic acid (106 mg, 0.50 mmol), and 2-chloro-1,3-dimethylimidazolidinium chloride (106 mg, 0.63 mmol). The reaction mixture was agitated for 18 h. The solution was drained and the resin washed with DCM then MeOH (3 cycles), followed by DCM (3×).

Step C:

To the resin from step B was added DCE (2 mL), piperidine (107 mg, 1.26 mmol), and LiClO$_4$ (13 mg, 0.13 mmol). The reaction was agitated for 20 h. The solution was drained and the resin washed with DCM then MeOH (3 cycles), followed by DCM (3×).

Step D:

To the resin from step C was added 50% TFA/DCM (2.5 mL). The resin was agitated for 1 h and the filtrate collected. The resin was washed with 2% TFA/DCM (2×1.5 mL). The combined filtrates were concentrated to a residue and purified by reverse-phase chromatography to furnish the product, 4-Benzyl-N-(2-hydroxy-3-piperidin-1-yl-propyl)-benzamide (13 mg, 0.028 mmol) as a trifluoroacetate salt. MS m/z (MH$^+$) calcd 353.2, found 353.4.

The invention claimed is:

1. A compound of formula (Ia):

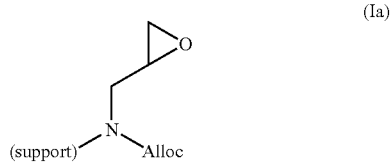

(Ia)

wherein (support) is selected from the group consisting of amine based polystyrene resins.

2. The compound according to claim 1 wherein (support) is a Rink type resin.

3. The compound according to claim 1 wherein (support) is Rink-AM resin.

* * * * *